(12) United States Patent
Takahashi

(10) Patent No.: US 11,871,907 B2
(45) Date of Patent: Jan. 16, 2024

(54) ILLUMINATION OPTICAL SYSTEM FOR ENDOSCOPE, OPTICAL ADAPTOR AND ENDOSCOPE

(71) Applicant: Evident Corporation, Nagano (JP)

(72) Inventor: Susumu Takahashi, Iruma (JP)

(73) Assignee: Evident Corporation, Nagano (JP)

( * ) Notice: Subject to any disclaimer, the term of this patent is extended or adjusted under 35 U.S.C. 154(b) by 0 days.

(21) Appl. No.: 17/824,187

(22) Filed: May 25, 2022

(65) Prior Publication Data

US 2022/0378285 A1 Dec. 1, 2022

(30) Foreign Application Priority Data

May 28, 2021 (JP) .................................. 2021-090644
Jan. 31, 2022 (JP) .................................. 2022-013074

(51) Int. Cl.
*A61B 1/06* (2006.01)
*A61B 1/07* (2006.01)
*A61B 1/00* (2006.01)

(52) U.S. Cl.
CPC ........ *A61B 1/0684* (2013.01); *A61B 1/00096* (2013.01); *A61B 1/0615* (2013.01); *A61B 1/0623* (2013.01); *A61B 1/07* (2013.01)

(58) Field of Classification Search
CPC ............ A61B 1/00096; A61B 1/00163; A61B 1/00165; A61B 1/002; A61B 1/00177; A61B 1/00179; A61B 1/07; G02B 5/0215; G02B 5/0231
See application file for complete search history.

(56) References Cited

U.S. PATENT DOCUMENTS

| 6,424,786 | B1* | 7/2002 | Beeson | G02B 6/1221 |
| | | | | 385/146 |
| 2009/0046370 | A1* | 2/2009 | Chang | G02B 5/045 |
| | | | | 359/625 |
| 2009/0262428 | A1* | 10/2009 | Kurokawa | G02B 5/0231 |
| | | | | 359/599 |

(Continued)

FOREIGN PATENT DOCUMENTS

| JP | 2008-010321 A | 1/2008 |
| JP | 2010-217349 A | 9/2010 |

(Continued)

*Primary Examiner* — Aaron B Fairchild
*Assistant Examiner* — Julianna J Nicolaus
(74) *Attorney, Agent, or Firm* — Scully, Scott, Murphy & Presser, P.C.

(57) ABSTRACT

An illumination optical system for endoscope includes a rod lens as an optical element. The optical element includes a proximal end surface through which light enters and a distal end surface configured to emit the light. The distal end surface includes a diffusion region configured to diffuse emitted light. The diffusion region includes a plurality of concave portions and a plurality of peripheral regions surrounding the concave portions. Each concave portion includes a plurality of inclined surfaces as total reflection surfaces that are inclined with respect to the distal end surface. Each peripheral region includes a transmission surface configured to emit light totally reflected by the total reflection surfaces after passing through the proximal end surface and light not totally reflected by the total reflection surfaces.

15 Claims, 15 Drawing Sheets

(56) References Cited

U.S. PATENT DOCUMENTS

| | | | | |
|---|---|---|---|---|
| 2012/0200930 A1* | 8/2012 | Yamamoto | ............... | G02B 5/23 |
| | | | | 522/100 |
| 2013/0070478 A1* | 3/2013 | Edamitsu | .................. | F21V 5/02 |
| | | | | 362/311.06 |
| 2016/0320532 A1* | 11/2016 | Purchase | ................... | F21V 7/00 |
| 2019/0313891 A1* | 10/2019 | Oka | ..................... | G02B 5/0242 |
| 2022/0031145 A1 | 2/2022 | Takahashi | | |

FOREIGN PATENT DOCUMENTS

| | | | | |
|---|---|---|---|---|
| JP | 2010217349 A | * | 9/2010 | |
| JP | 2012-242508 A | | 12/2012 | |
| JP | 2015-226712 A | | 12/2015 | |
| WO | WO-2007049618 A1 | * | 5/2007 | ........... G02B 5/0226 |

* cited by examiner

ILLUMINATION OPTICAL SYSTEM FOR ENDOSCOPE, OPTICAL ADAPTOR AND ENDOSCOPE

CROSS REFERENCE TO RELATED APPLICATION

This application claims benefit of Japanese Application No. 2021-090644 filed in Japan on May 28, 2021 and Japanese Application No. 2022-013074 filed in Japan on Jan. 31, 2022, the entire contents of each of which are incorporated herein by their reference.

BACKGROUND OF THE INVENTION

1. Field of the Invention

The invention relates to an illumination optical system for endoscope, an optical adaptor and an endoscope, and particularly relates to an illumination optical system for an endoscope that includes an insertion portion configured to be inserted into a subject, an optical adaptor, and an endoscope that includes the illumination optical system.

2. Description of the Related Art

An endoscope is widely used in an industrial field and a medical field. The endoscope includes an insertion portion, and illumination light is emitted from a distal end portion of the insertion portion. Reflected light of the illumination light from an object is received by an observation window, and an object image is acquired, so that an object image of an interior of a subject is obtained as an endoscope image.

An illumination optical system including an optical element configured to diffuse light such that the illumination light has a desired light distribution angle is provided in an optical adaptor attached to the distal end portion of the insertion portion or in the distal end portion of the insertion portion.

A plurality of inclined surfaces are formed on an incident surface of the optical element, and the plurality of inclined surfaces diffuse light. By the diffusion, the illumination light having a desired light distribution angle is emitted from an emission surface of the optical element. For example, in an optical element disclosed in Japanese Patent Application Laid-Open Publication No. 2015-226712, a prism surface on which a plurality of prisms including a plurality of inclined surfaces are regularly formed on the incident surface of the optical element is provided.

SUMMARY OF THE INVENTION

An illumination optical system for endoscope in an aspect of the invention is an illumination optical system for endoscope that includes an insertion portion configured to be inserted into a subject, in which the illumination optical system for endoscope includes an optical element including an incident surface through which light enters as incident light and an emission surface configured to emit the light as illumination light, the emission surface includes a diffusion region configured to diffuse the light emitted, the diffusion region includes a plurality of concave portions and a plurality of peripheral regions, the plurality of concave portions and the plurality of peripheral regions being arrayed on the emission surface, each of the plurality of concave portions includes a plurality of total reflection surfaces inclined with respect to the emission surface, each of the plurality of total reflection surfaces being configured to totally reflect the incident light, at least one of the plurality of total reflection surfaces is inclined at a first angle with respect to the emission surface, each of the plurality of peripheral regions is formed so as to surround the plurality of total reflection surfaces, and includes a transmission surface configured to transmit and emit I: reflected light totally reflected by the plurality of total reflection surfaces after passing through the incident surface, and II: the incident light not totally reflected by the plurality of total reflection surfaces after passing through the incident surface.

An optical adaptor in an aspect of the invention is an optical adaptor that can be attached to a distal end portion of an insertion portion configured to be inserted into a subject, in which the optical adaptor includes an optical element including an incident surface through which light enters as incident light and an emission surface configured to emit the light as illumination light, the emission surface includes a diffusion region configured to diffuse the light emitted, the diffusion region includes a plurality of concave portions and a plurality of peripheral regions, the plurality of concave portions and the plurality of peripheral regions being arrayed on the emission surface, each of the plurality of concave portions includes a plurality of total reflection surfaces inclined with respect to the emission surface, each of the plurality of total reflection surfaces being configured to totally reflect the incident light, at least one of the plurality of total reflection surfaces is inclined at a first angle with respect to the emission surface, each of the plurality of peripheral regions is formed so as to surround the plurality of total reflection surfaces, and includes a transmission surface configured to transmit and emit I: reflected light totally reflected by the plurality of total reflection surfaces after passing through the incident surface, and II: the incident light not totally reflected by the plurality of total reflection surfaces after passing through the incident surface.

An endoscope in an aspect of the invention is an endoscope including: an illumination optical system for endoscope; and an insertion portion configured to be inserted into a subject, in which the illumination optical system for endoscope includes an optical element including an incident surface through which light enters as incident light and an emission surface configured to emit the light as illumination light, the emission surface includes a diffusion region configured to diffuse the light emitted, the diffusion region includes a plurality of concave portions and a plurality of peripheral regions, the plurality of concave portions and the plurality of peripheral regions being arrayed on the emission surface, each of the plurality of concave portions includes a plurality of total reflection surfaces inclined with respect to the emission surface, each of the plurality of total reflection surfaces being configured to totally reflect the incident light, at least one of the plurality of total reflection surfaces is inclined at a first angle with respect to the emission surface, each of the plurality of peripheral regions is formed so as to surround the plurality of total reflection surfaces, and includes a transmission surface configured to transmit and emit I: reflected light totally reflected by the plurality of total reflection surfaces after passing through the incident surface, and II: the incident light not totally reflected by the plurality of total reflection surfaces after passing through the incident surface.

DETAILED DESCRIPTION OF THE PREFERRED EMBODIMENTS

An Embodiment of the invention will be described below with reference to the drawings.

Note that in each figure to be used for following descriptions, a scale is different for each component element for obtaining a size allowing each component element to be recognized on the figure, and the invention is not limited only to quantities of component elements, shapes of component elements, proportions of sizes of component elements and relative position relations of component elements that are described in the figures.

(Configuration of Endoscope Apparatus)

Figure 1:
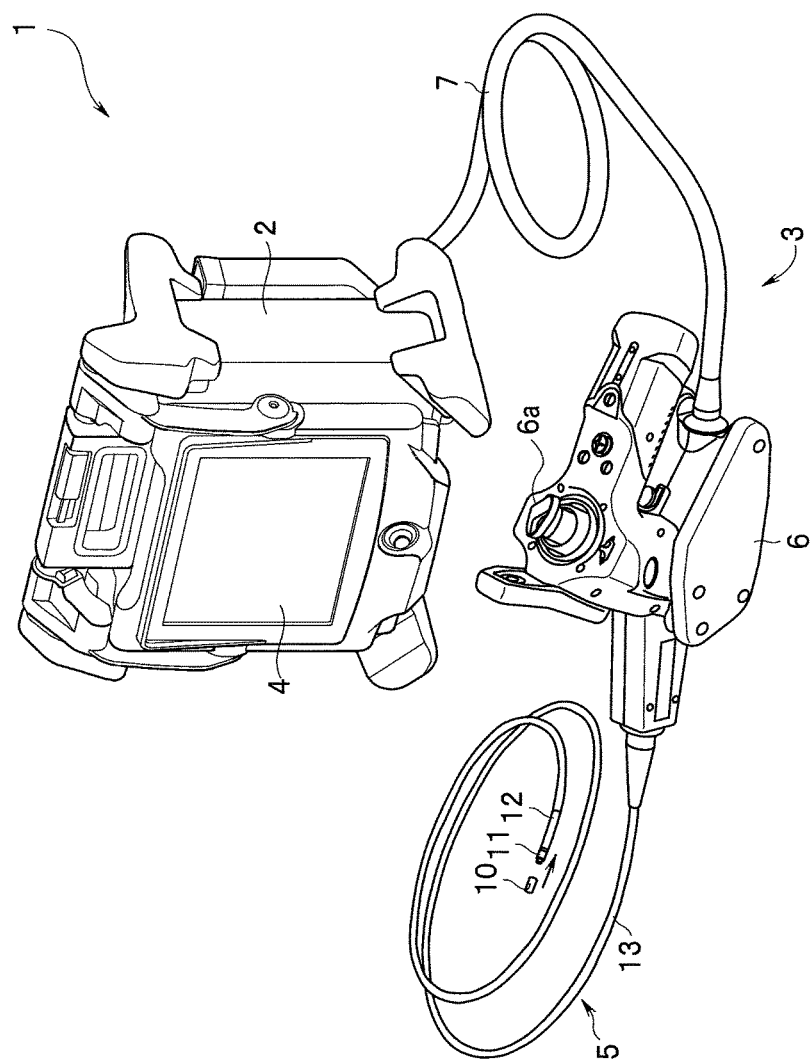
FIG. 1 is a configuration diagram showing a configuration of an endoscope apparatus according to an embodiment of the invention.

FIG. 1 is a configuration diagram showing a configuration of an endoscope apparatus according to the embodiment.

As shown in FIG. 1, an endoscope apparatus 1 is configured to include an apparatus body 2 having functions such as a video processor and an endoscope 3 connected to the apparatus body 2. The apparatus body 2 includes a display unit 4 on which an endoscope image, an operation menu and others are displayed, as exemplified by a liquid crystal panel (LCD). On the display unit 4, a touch panel may be provided.

The endoscope 3 is configured to include an insertion portion 5 as an endoscope insertion portion configured to be inserted into a subject, an operation portion 6 continuously provided at a proximal end of the insertion portion 5, and a universal code 7 extending from the operation portion 6. The endoscope 3 is detachable to the apparatus body 2 through the universal code 7.

The insertion portion 5 is configured to include a distal end portion 11, a bending portion 12 and a long flexible portion 13, in an order from a distal end side. The bending portion 12 is continuously provided at a proximal end of the distal end portion 11, and is configured to be capable of being bent in upward, downward, leftward and rightward directions, for example. The flexible portion 13 is continuously provided at a proximal end of the bending portion 12, and has flexibility.

As shown by an arrow, an optical adaptor 10 for front view can be attached to the distal end portion 11, in a detachable manner. For example, the endoscope 3 becomes a front-viewing endoscope by attaching the optical adapter 10 for front view to the distal end portion 11. In other words, the optical adaptor 10 can be attached to the distal end portion 11 of the insertion portion 5 of the endoscope 3. The optical adaptor 10 is attached depending on an examination subject, an examination purpose and the like. Consequently, the endoscope apparatus 1 can be used w % bile the optical adaptor 10 is not attached to the distal end portion 11. Note that the optical adaptor 10 may be an optical adaptor for side view, oblique view or the like, without being limited to the optical adaptor for the front view.

A bending joystick 6a configured to bend the bending portion 12 in the upward, downward, leftward and rightward directions is provided on the operation portion 6. A user can bend the bending portion 12 in a desired direction by performing an inclining operation of the bending joystick 6a. Further, on the operation portion 6, buttons configured to give instructions of endoscope functions, for example, various operation buttons such as a freeze button, a bending lock button and a recording instruction button are provided in addition to the bending joystick 6a.

Note that the user may give instructions of various operations of the endoscope apparatus 1 by operating the touch panel in the case of the configuration in which the touch panel is provided on the display unit 4.

An endoscope image picked up by an image pickup device 23 (FIG. 3 and FIG. 5) of an image pickup unit provided in the distal end portion 11 is displayed on the display unit 4 of the apparatus body 2. Further, various circuits such as a control unit (not illustrated) configured to perform image processing and various controls and a recording apparatus configured to record a processed image in a memory (not illustrated) are provided within the apparatus body 2.

Figure 2:
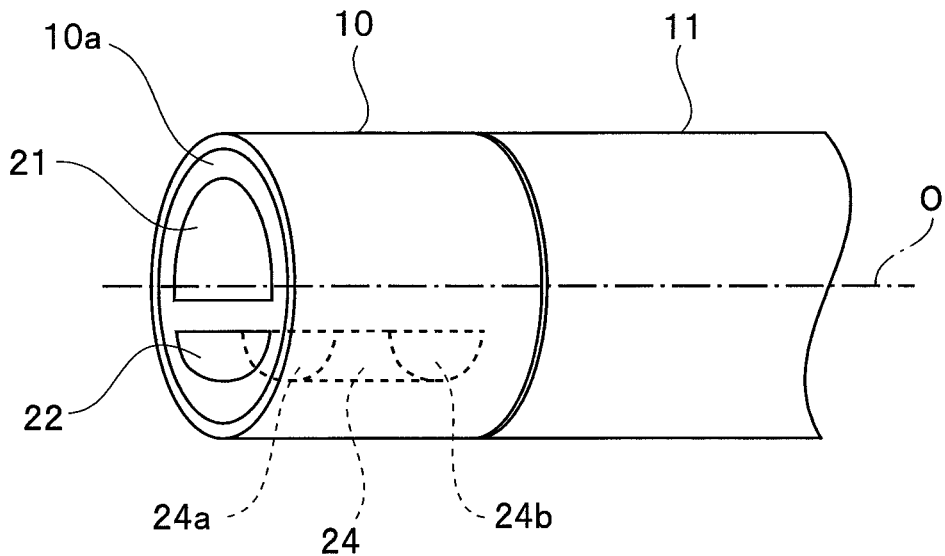
FIG. 2 is a perspective view of a distal end portion to which an optical adaptor is attached according to the embodiment of the invention.
Figure 3:
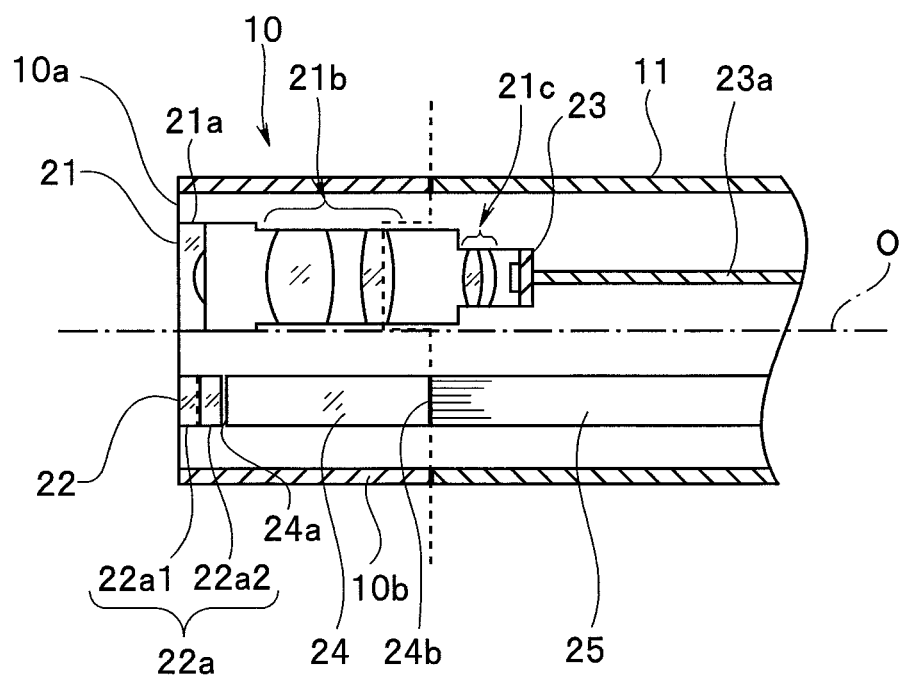
FIG. 3 is a sectional view of the distal end portion to which the optical adaptor is attached according to the embodiment of the invention.

FIG. 2 is a perspective view of the distal end portion 11 to which the optical adaptor 10 is attached. FIG. 3 is a sectional view of the distal end portion 11 to which the optical adaptor 10 is attached. FIG. 3 shows a section of the distal end portion 11 along a longitudinal axis O of the insertion portion 5. In FIG. 3, a left side of a dotted line is the optical adaptor 10, and a right side of the dotted line is the distal end portion 11.

The optical adaptor 10 has a cylindrical shape. An observation window 21 and an illumination window 22 are provided on a distal end surface 10a of the optical adaptor 10. The observation window 21 and the illumination window 22 have partial circular shapes when the optical adaptor 10 is viewed from the distal end side. Particularly, the illumination window 22 has an elongate semicircular shape.

The observation window 21 is configured by a cover glass 21a. The cover glass 21a also functions as a concave lens of the observation window. On a rear side of the cover glass 21a, a lens configuring a lens group 21b that configures an observation optical system is provided in a housing 10b of the optical adaptor 10.

The distal end portion 11 of the insertion portion 5 includes an unillustrated distal end rigid member, and a lens 21c configuring the observation optical system and the image pickup device 23 are built in the distal end rigid member. For example, the image pickup device 23 is a CCD image sensor or a CMOS image sensor. When the optical adaptor 10 is attached to the distal end portion 11 of the insertion portion 5, the lens in the optical adaptor 10 and the lens in the distal end portion 11 form an image pickup optical system for the image pickup device 23, namely, the observation optical system. Consequently, the cover glass 21a, the lens group 21b and the lens 21c configure the observation optical system. A signal wire 23a extends from the image pickup device 23. The signal wire 23a is connected to a circuit board in the apparatus body 2.

The illumination window 22 emits illumination light. Reflected light from an object enters the observation window 21. The light from the object forms an object image on an image pickup surface of the image pickup device 23 through the observation optical system.

The illumination window 22 is configured by a cover glass 22a. The cover glass 22a includes two glasses 22a1, 22a2. The two glasses 22a1, 22a2 are pasted to each other by an adhesive.

For example, a proximal end surface of the glass 22a1 is a grey surface (shown by a dotted line). A distal end surface of the glass 22a1 is a flat surface. Each of a proximal end surface and distal end surface of the glass 22a2 is a flat surface. The two glasses 22a1, 22a2 are bonded and fixed by the adhesive, so as to sandwich the grey surface. The grey surface randomly diffuses light, and eliminates an uneven light distribution due to light distribution regularity of a diffusion device having a later-described diffusion structure. For example, each of the refraction indexes of the glasses 22a1, 22a2 is 1.52, and the refraction index of the adhesive is 1.56. By using members having slightly different refraction indexes as the glasses 22a1, 22a2 and the adhesive, the uneven light distribution is eliminated while an excessive scattering is prevented. Note that when the securement of the quantity of light has priority over the elimination of the uneven light distribution, the grey surface does not need to be provided on the proximal end surface of the glass 22a1.

Light that enters the proximal end surface of the glass 22a2 is emitted from the distal end surface of the glass 22a1.

Note that the cover glass 22a may be disposed so as to be arrayed in an order of the glass 22a1 and the glass 22a2 from the proximal end side. In that case, the glasses 22a1, 22a2 are disposed so as to be away from each other, such that an air layer is formed between the glass 22a2 on the distal end surface side and the glass 22a1 on the proximal end side.

A rod lens 24 having a partial column shape is arranged in the housing 10b of the optical adaptor 10 on a rear side of the cover glass 22a. The rod lens 24 is made of a transparent glass or plastic. A light guide 25 that is a bundle of optical fibers is arranged in the insertion portion 5. A distal end surface of the light guide 25 is disposed at the distal end portion 11. When the optical adaptor 10 is attached to the distal end portion 11, the distal end surface of the light guide 25 faces a proximal end surface 24b of the rod lens 24.

Light from a light source in the apparatus body 2 enters a proximal end surface of the light guide 25. Light emitted from the distal end surface of the light guide 25 enters the proximal end surface 24b of the rod lens 24. The light that enters the proximal end surface 24b of the rod lens 24 passes through the rod lens 24, and is emitted from the distal end surface 24a of the rod lens 24, and the distal end surface 24a of the rod lens 24 has a diffusion structure for diffusing the emitted light.

In other words, the rod lens 24 is an optical element including the proximal end surface 24b that is an incident surface through which light enters as incident light and the distal end surface 24a that is an emission surface configured to emit light as illumination light.

In the embodiment, the endoscope 3 is a front-viewing endoscope, and the proximal end surface 24b that is the light incident surface of the rod lens 24 and the distal end surface 24a that is the light emission surface are parallel.

Diffused light from the distal end surface 24a of the rod lens 24 enters the cover glass 22a, and is emitted from the illumination window 22.

The endoscope 3 shown in FIG. 2 and FIG. 3 includes the illumination window 22 having an elongate semicircular shape, but the illumination window 22 may have a ring shape.

Figure 4:
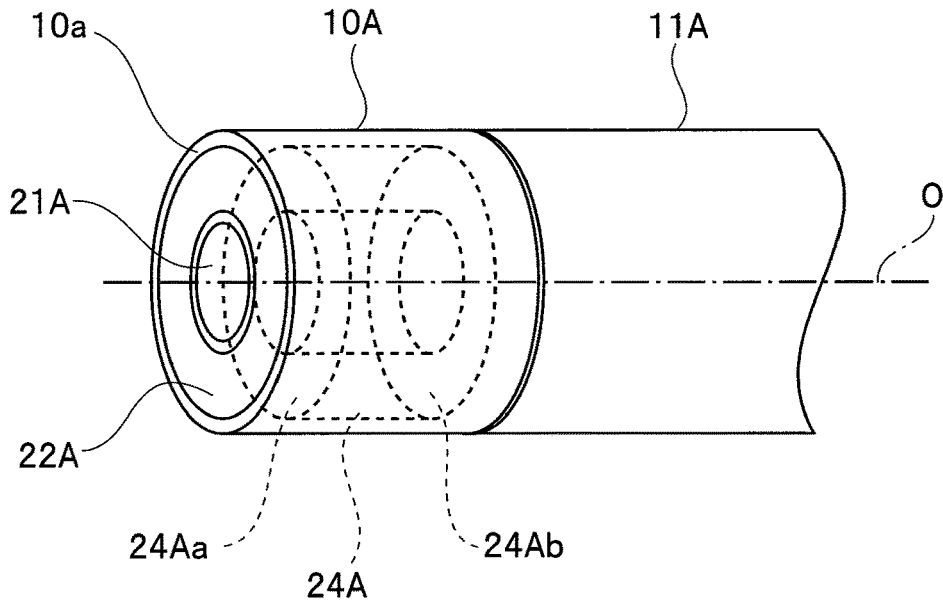
FIG. 4 is a perspective view of a distal end portion to which an optical adaptor including a ring-shaped illumination window is attached according to the embodiment of the invention.
Figure 5:
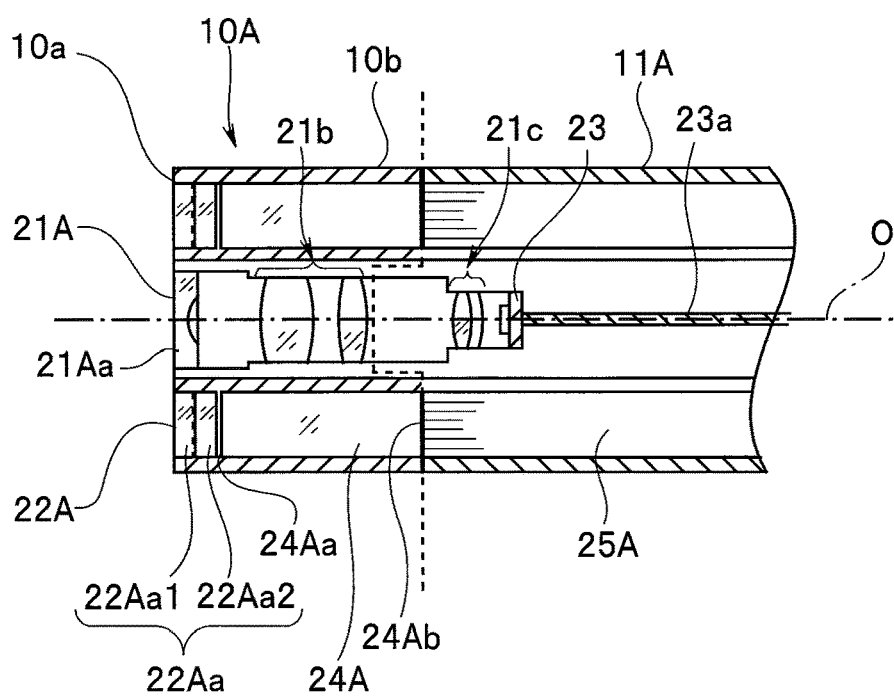
FIG. 5 is a sectional view of the distal end portion to which the optical adaptor including the ring-shaped illumination window is attached according to the embodiment of the invention.

FIG. 4 is a perspective view of a distal end portion 11A to which an optical adaptor 10A including a ring-shaped illumination window 22 is attached. FIG. 5 is a sectional view of the distal end portion 11A to which the optical adaptor 10A including the ring-shaped illumination window 22 is attached. FIG. 5 shows a section of the distal end portion 11 along the longitudinal axis O of the insertion portion 5. In FIG. 5, a left side of a dotted line is the optical adaptor 10A, and a right side of the dotted line is the distal end portion 11A.

The optical adaptor 10A in FIG. 4 and FIG. 5 has a cylindrical shape. An observation window 21A and an illumination window 22A are provided on a distal end surface 10a of the optical adaptor 10A. The observation window 21A has a circular shape when the optical adaptor 10A is viewed from the distal end side. The illumination window 22A has a ring shape when the optical adaptor 10A is viewed from the distal end side.

The observation window 21A is configured by a cover glass 21Aa. On a rear side of the cover glass 21Aa, a lens configuring a lens group 21b is provided in a housing 10b of the optical adaptor 10A.

The distal end portion 11A of the insertion portion 5 includes an unillustrated distal end rigid member, and a lens 21c configuring an observation optical system and the image pickup device 23 are built in the distal end rigid member. In other words, when the optical adaptor 10A is attached to the insertion portion 5, the observation optical system is configured by the cover glass 21a, the lens group 21b and the lens 21c.

The illumination window 22A is configured by a ring-shaped cover glass 22Aa. The cover glass 22Aa includes two ring-shaped glasses 22Aa1, 22Aa2.

For example, a proximal end surface of the glass 22Aa1 is a grey surface (shown by a dotted line). A distal end surface of the glass 22Aa1 is a flat surface. Each of a proximal end surface and distal end surface of the glass 22Aa2 is a flat surface. The two glasses 22Aa1, 22Aa2 are bonded and fixed by an adhesive, so as to sandwich the grey surface. For example, each of the refraction indexes of the glasses 22Aa1, 22Aa2 is 1.88, and the refraction index of the adhesive is 1.56. By using members having slightly different refraction indexes as the glasses 22Aa1, 22Aa2 and the adhesive, the uneven light distribution is eliminated while the excessive scattering is prevented.

In the cover glass 22Aa, light that enters the proximal end surface of the glass 22Aa is emitted from the distal end surface of the glass 22Aa1.

Note that the cover glass 22Aa may be disposed so as to be arrayed in an order of the glass 22Aa1 and the glass 22Aa2 from the proximal end side. In that case, the glasses 22Aa1, 22Aa2 are disposed so as to be away from each other, such that an air layer is formed between the glass 22Aa2 on the distal end surface side and the glass 22Aa1 on the proximal end side.

A rod lens 24A having a cylindrical shape is arranged in the housing 10b of the optical adaptor 10A on a rear side of the cover glass 22Aa. A light guide 25A that is a bundle of optical fibers is arranged in the insertion portion 5. At a distal end part of the light guide 25A, a distal end surface is formed in a ring shape, and is disposed at the distal end portion 11A. When the optical adaptor 10A is attached to the distal end portion 11A, the distal end surface of the light guide 25A faces a proximal end surface 24Ab of the rod lens 24A.

Light from the light source in the apparatus body 2 enters a proximal end surface of the light guide 25A. Light emitted from the distal end surface of the light guide 25A enters the proximal end surface 24Ab of the rod lens 24A. The light that enters the proximal end surface 24Ab of the rod lens 24A passes through the rod lens 24A, and is emitted from the distal end surface 24Aa of the rod lens 24A. The distal end surface 24Aa of the rod lens 24A has a diffusion structure for diffusing the emitted light.

In other words, the rod lens 24A is an optical element including the proximal end surface 24Ab that is an incident surface through which light enters as incident light and the distal end surface 24Aa that is an emission surface configured to emit light as illumination light.

Diffused light from the distal end surface 24Aa of the rod lens 24A enters the cover glass 22Aa, and is emitted from the illumination window 22A.

As described above, the rod lens 24 or 24A has the diffusion structure on the distal end surface 24a or 24Aa. Next, the diffusion structure will be described.

Note that the rod lens 24, 24A having the diffusion structure on the distal end surface 24a, 24Aa is provided in the optical adaptor 10, 10A in the above-described example. However, without being limited to this, the rod lens 24, 24A may be provided in the distal end portion 11, 11A of the insertion portion 5 of the endoscope 3 that allows the observation of the object with no optical adaptor 10, 10A. In other words, the rod lens 24, 24A having the diffusion structure may be provided on a rear side (a proximal end side in the case of the front-viewing endoscope) of the illumination window 22, 22A of the distal end portion 11, 11A.

Next, the diffusion structure of the rod lens 24 will be described.

Figure 6:
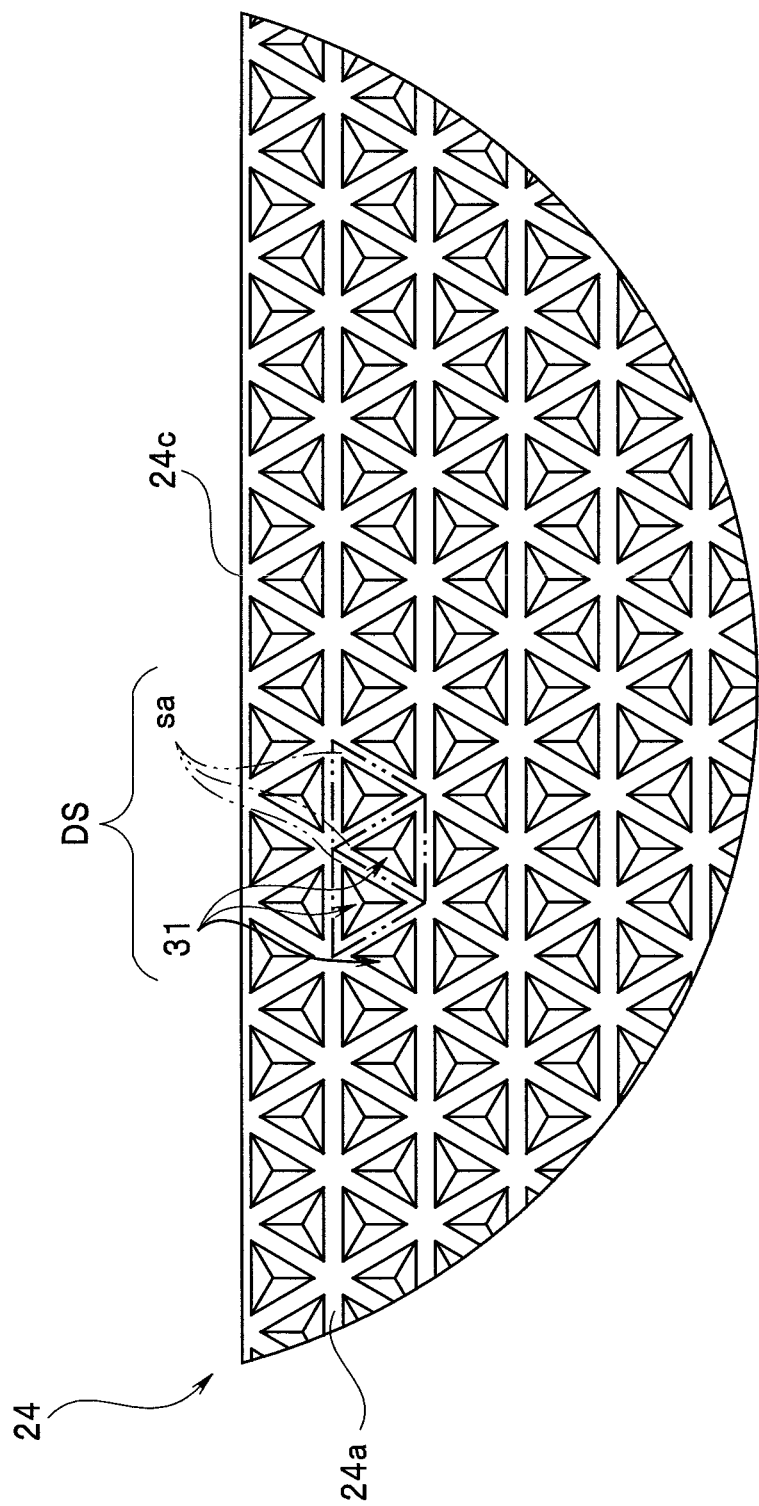
FIG. 6 is a diagram of a rod lens as viewed from a distal end side according to the embodiment of the invention.
Figure 7:
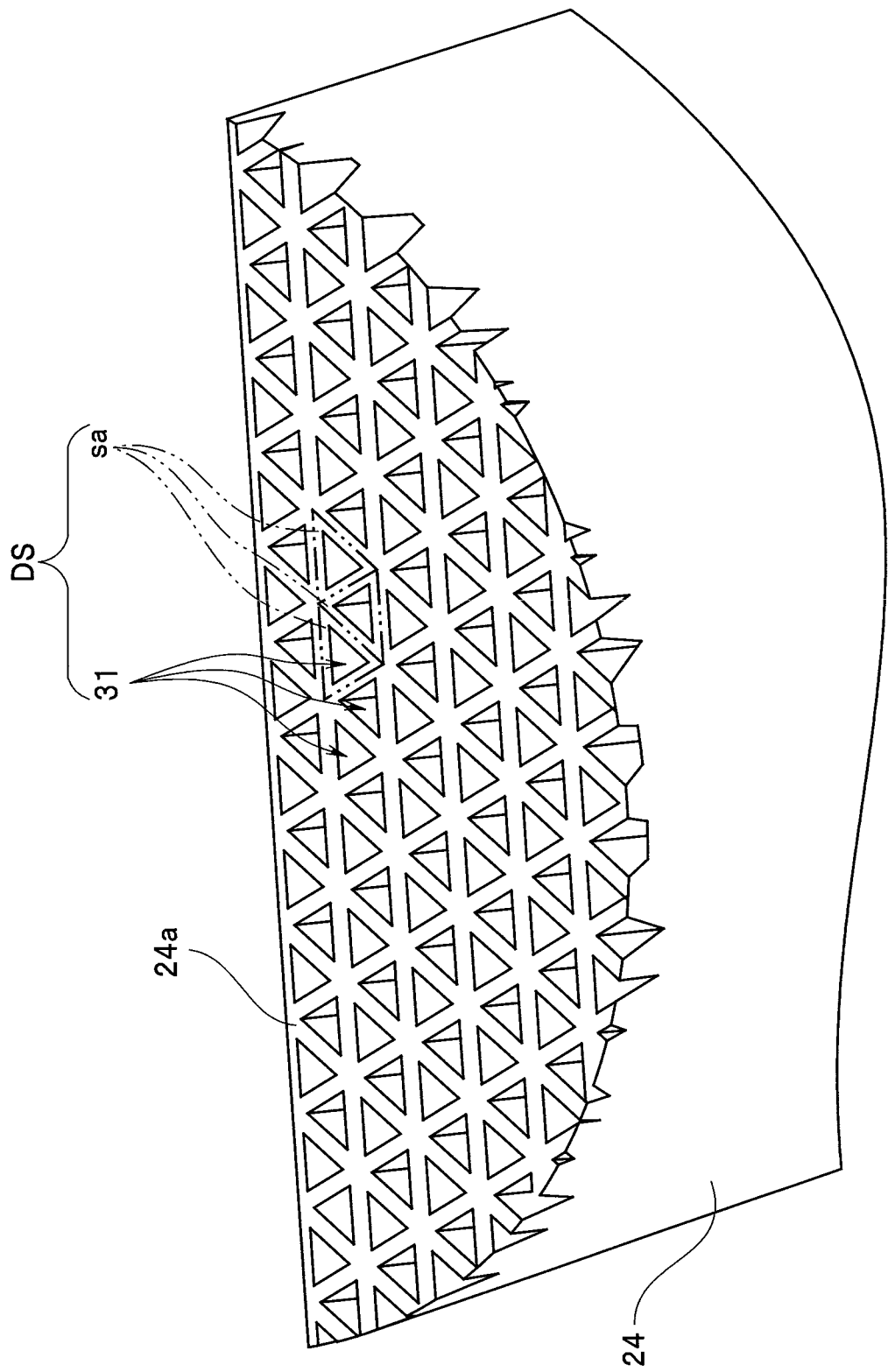
FIG. 7 is a perspective view of a distal end part of the rod lens as viewed diagonally from the distal end side according to the embodiment of the invention.

FIG. 6 is a diagram of the rod lens 24 as viewed from the distal end side. FIG. 7 is a perspective view of a distal end part of the rod lens 24 as viewed diagonally from the distal end side.

A plurality of concave portions 31 are formed on the distal end surface 24a of the rod lens 24. Each concave portion 31 has a polygonal pyramid shape. In the embodiment, an opening of each concave portion 31 has a regular triangular shape, and each concave portion 31 has a trigonal pyramid shape. A peripheral region sa shown by a two-dot chain line is provided around the opening of each concave portion 31 on the distal end surface 24a.

In other words, the distal end surface 24a that is the emission surface includes a diffusion region DS configured to diffuse the emitted light. The diffusion region DS includes a plurality of concave portions 31 and a plurality of peripheral regions sa that are arrayed on the distal end surface 24a.

Figure 8:
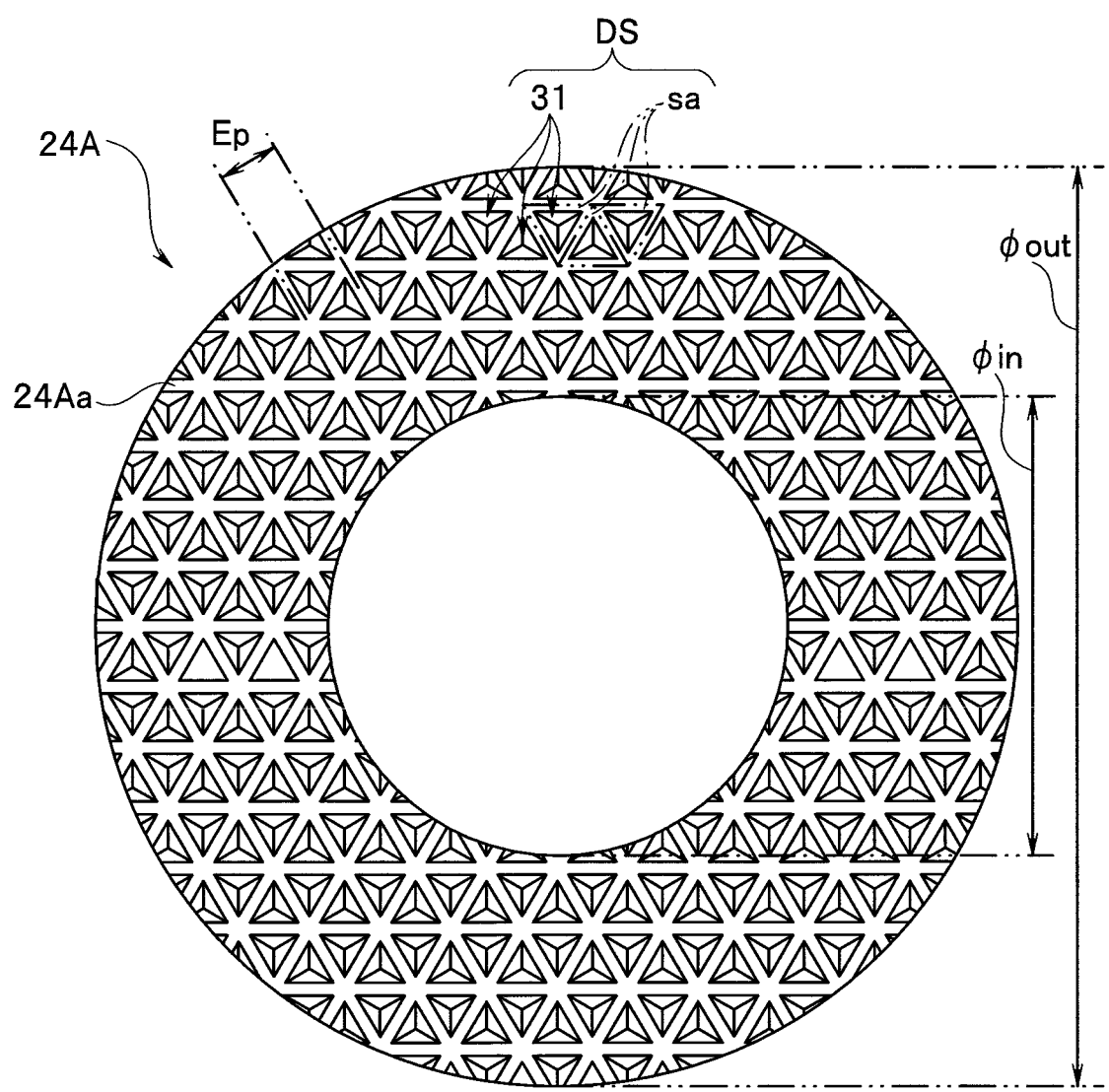
FIG. 8 is a diagram of a cylindrical rod lens as viewed from the distal end side according to the embodiment of the invention.

FIG. 8 is a diagram of the cylindrical rod lens 24A as viewed from the distal end side. Also on the distal end surface 24Aa of the rod lens 24A, a plurality of concave portion 31 having the same shape as the shape in FIG. 6 and FIG. 7 are formed, and a peripheral region sa shown by a two-dot chain line is provided around the opening of each concave portion 31.

Next, the shape of the concave portion 31 will be described.

Figure 9:
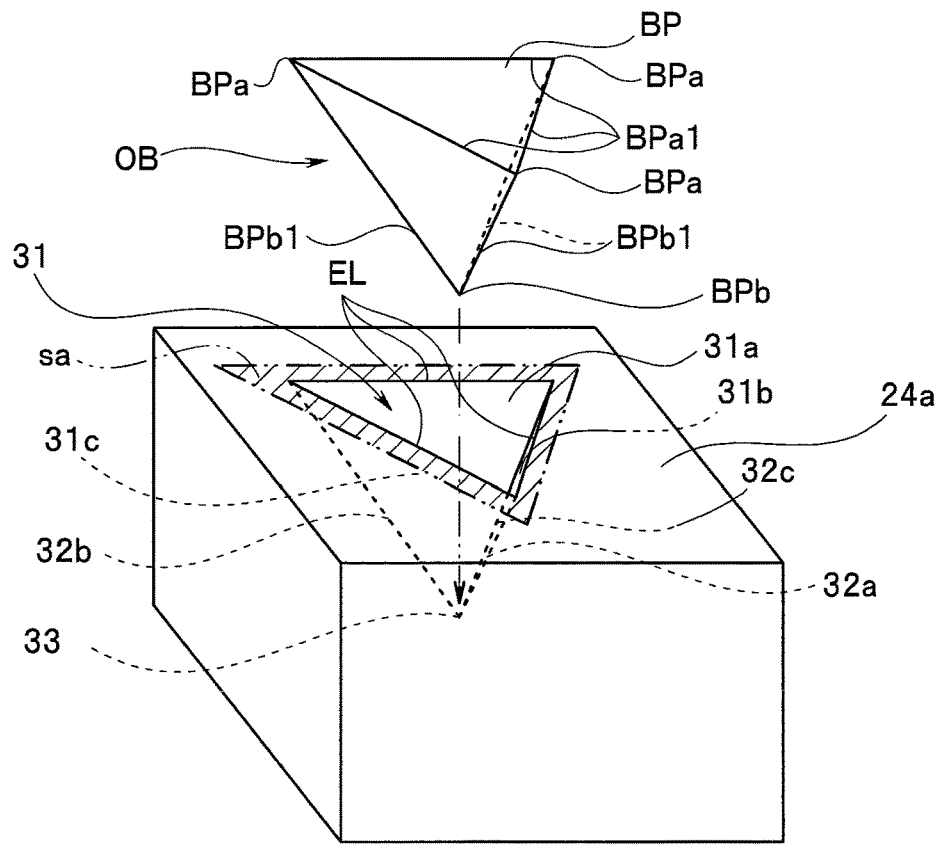
FIG. 9 is a diagram for describing a shape of a concave portion according to the embodiment of the invention.

FIG. 9 is a diagram for describing the shape of the concave portion 31. The concave portion 31 has a shape in which a physical object OB having a regular trigonal pyramid shape is fit. The physical object OB has a regular trigonal pyramid shape in which the shape of a section parallel to a bottom surface BP is a regular triangle. The bottom surface BP of the physical object OB has a regular triangular shape. The bottom surface BP includes three apexes BPa and three sides BPa1. The physical object OB includes a fourth apex BPb and three sides BPb1 connecting the three apexes BPa and the apex BPb.

When the physical object OB is reversed and is fit in the concave portion 31, the bottom surface BP having a regular triangular shape is flush with the distal end surface 24a, 24Aa of the rod lens 24, 24A (the rod lens 24 will be described below as an example, but the same goes for the rod lens 24A).

In other words, as shown in FIG. 9, each concave portion 31 has such a shape that the bottom surface BP is parallel to the distal end surface 24a of the rod lens 24 when the physical object OB that is the regular trigonal pyramid is reversed and is fit in the concave portion 31.

Consequently, the concave portion 31 includes three inclined surfaces 31a, 31b, 31c. Each of the inclined surfaces 31a, 31b, 31c has an isosceles triangular shape (or a regular triangular shape) as viewed in a perpendicular direction to each of the inclined surfaces 31a, 31b, 31c. A point 33 where border lines 32a, 32b, 32c of pairs of two adjacent inclined surfaces are joined is at a deepest portion of the concave portion 31.

Each concave portion 31 has a polygonal pyramid shape (a regular trigonal pyramid) in which the apex is at the deepest portion and the bottom surface BP having a regular polygonal shape (a regular triangular shape in the embodiment) is an opening, and when the distal end surface 24a is viewed in a perpendicular direction to the distal end surface 24a, the point 33 that is the apex is at a barycenter position of the regular polygon (the regular triangle in the embodiment).

The border line 32a faces the inclined surface 31a, the border line 32b faces the inclined surface 31b, and the border line 32c faces the inclined surface 31c. Angles of the inclined surfaces 31a, 31b, 31c with respect to the distal end surface 24a are equal.

Note that the deepest portion of the concave portion 31 is the point 33 in the embodiment, but may be a flat surface portion parallel to the distal end surface 24a. In that case, the concave portion 31 has a trigonal pyramid trapezoidal shape.

The peripheral region sa is provided so as to surround the opening of the concave portion 31. The peripheral region sa is a part of the distal end surface 24a that is the emission surface.

Figure 10:
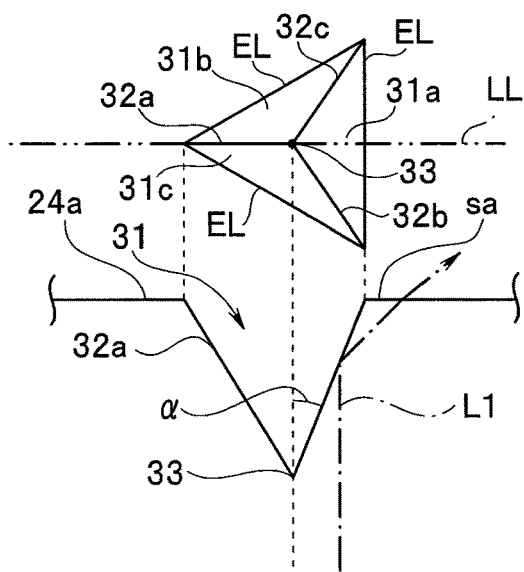
FIG. 10 is a sectional view showing a section shape of the concave portion according to the embodiment of the invention.

FIG. 10 is a sectional view showing a section shape of the concave portion 31. A lower side in FIG. 10 shows a section of the concave portion 31 along a plane LL that includes the border line 32a and that is orthogonal to the distal end surface 24a. In the case where the material of the rod lens 24 is glass and a refraction index n is in a range from 1.4 to 2.0, an inclination angle $\alpha$ of the inclined surface 31a with respect to a direction orthogonal to the distal end surface 24a on the plane LL is an angle in a range that is 5 degrees or larger and is smaller than 20 degrees. The inclination angles of the other inclined surfaces 31b, 31c are the same as the inclination angle $\alpha$ of the inclined surface 31a, and is an angle in a range that is 5 degrees or larger and is smaller than 20 degrees. In other words, the angle (first angle) of each of the inclined surfaces 31a, 31b, 31c with respect to the distal end surface 24a is an angle in a range that is 85 degrees or smaller and is larger than 70 degrees, namely, $70°<(90-\alpha) \leq 85°$ is satisfied.

Some of light from the proximal end surface 24b of the rod lens 24 to the distal end surface 24a is totally reflected by each of the inclined surfaces 31a, 31b, 31c. The totally reflected light L1 is emitted from the peripheral region sa of the concave portion 31 that is a transmission region. In other words, each concave portion 31 includes a plurality of (three in the embodiment) inclined surfaces 31a, 31b, 31c that are total reflection surfaces to totally reflect the incident light. Each of the inclined surfaces 31a, 31b, 31c is a total reflection surface that is inclined at an angle $(90-\alpha)$ with respect to the distal end surface 24a that is the emission surface.

The opening of each concave portion 31 has a regular triangular shape. The opening includes three sides EL. The peripheral region sa is provided so as to surround the three sides EL of the opening of each concave portion 31. Each peripheral region sa is a transmission surface formed so as to surround the plurality of (three in the embodiment) inclined surfaces 31a, 31b, 31c and configured to transmit and emit reflected light totally reflected by the inclined surfaces 31a, 31b, 31c and light not totally reflected by the inclined surfaces 31a, 31b, 31c from the proximal end surface 24b.

The diffusion region DS is formed by providing a plurality of concave portions 31, one of which is shown in FIG. 9, and a plurality of peripheral regions sa, each of which surrounds the concave portion 31, on the distal end surface 24a that is the emission surface, as shown in FIG. 6 to FIG. 8.

In other words, each concave portion 31 has a trigonal pyramid shape in which the apex BPb is at the deepest portion and in which the bottom surface BP having a regular triangular shape is the opening, and the plurality of total reflection surfaces are the three flat surfaces (the inclined surfaces 31a, 31b, 31c) that are of the trigonal pyramid shape and that are other than the bottom surface.

In the case of FIG. 6, in the plurality of concave portions 31, one side of the three sides EL is formed on the distal end surface 24a of the rod lens 24 at regular intervals, so as to be parallel to a straight line portion 24c of the distal end surface 24a having a partial circular shape. Furthermore, the plurality of concave portions 31 are disposed on the distal end surface 24a, such that two adjacent sides EL of two adjacent concave portions 31 are parallel to each other and the interval of two adjacent sides EL of two adjacent concave portions 31 is equal among all concave portions 31.

Figure 11:
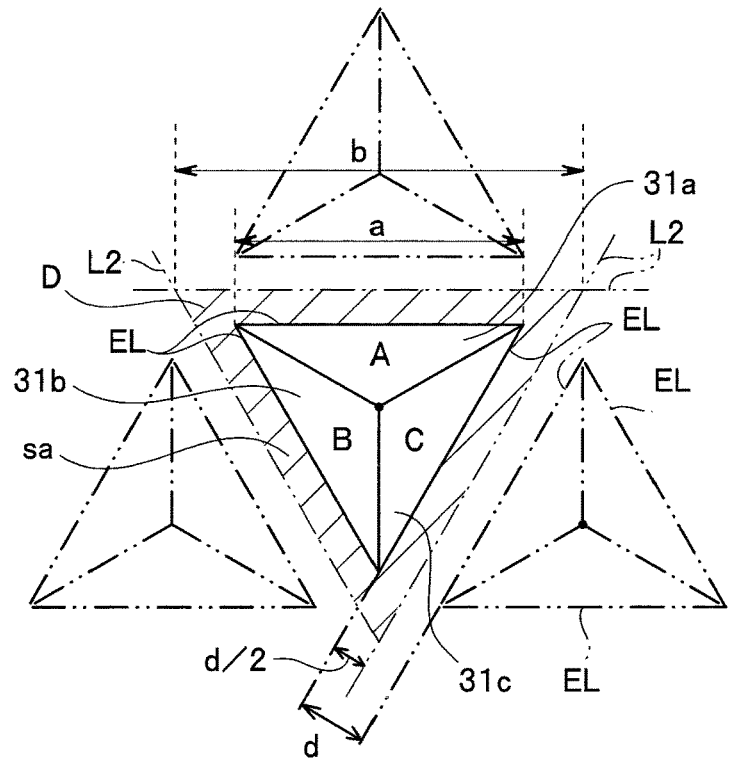
FIG. 11 is a diagram for describing a light transmission region of each concave portion according to the embodiment of the invention.

FIG. 11 is a diagram for describing a light transmission region of each concave portion 31. FIG. 11 is a plan view of the concave portion 31 when the distal end surface 24a is viewed in the perpendicular direction to the distal end surface 24a.

Three concave portions 31 (shown by two-dot chain lines) are formed around one concave portion 31 (shown by solid lines), such that two adjacent sides EL of two adjacent concave portions 31 are parallel as described above. On the distal end surface 24a, regions other than the plurality of concave portions 31 are the plurality of peripheral regions sa.

Figure 12:
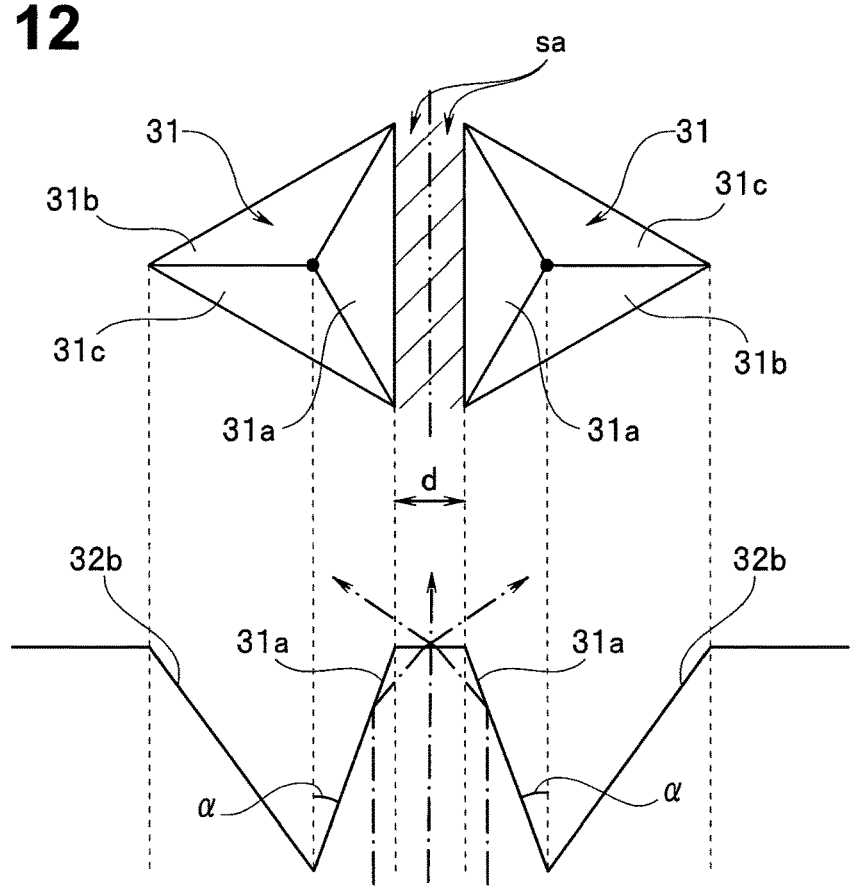
FIG. 12 is a diagram for describing a peripheral region from which totally reflected light is emitted according to the embodiment of the invention.

FIG. 12 is a diagram for describing the peripheral region sa from which the totally reflected light is emitted. Light totally reflected by one inclined surface 31a of one concave portion 31 is emitted from a peripheral region sa (shown by oblique lines) having a width (d/2). Light not totally reflected by the inclined surface 31a (or 31b or 31c) and directly reaching from the proximal end surface 24b to the peripheral region sa is also emitted from the peripheral region sa (shown by oblique lines).

Note that the peripheral region sa surrounding the inclined surfaces 31a. 31b, 31c is a surface parallel to the distal end surface 24a of the rod lens 24, but may include an inclined portion.

Figure 13:
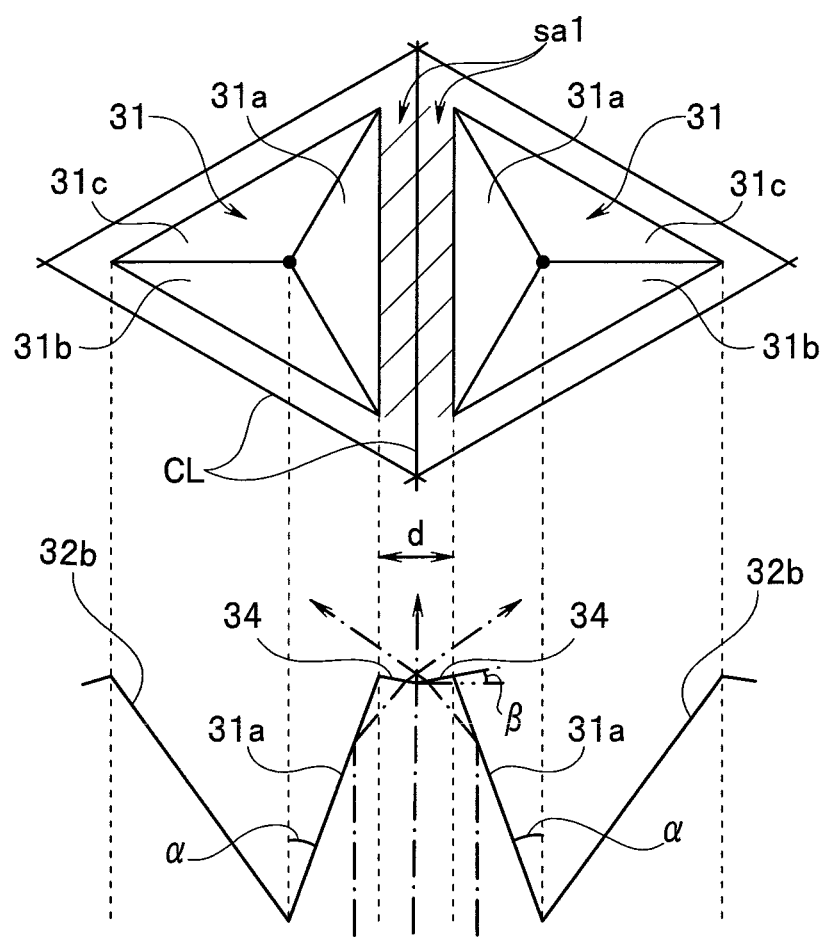
FIG. 13 is a diagram for describing a peripheral region including an inclined surface according to the embodiment of the invention.

FIG. 13 is a diagram for describing a peripheral region sa1 including an inclined surface. The peripheral region sa1 is an inclined surface provided so as to surround the opening of the concave portion 31. Consequently, there are two inclined surfaces 34 between the two parallel sides EL of two adjacent concave portions 31. The inclined surface provided so as to surround the opening of the concave portion 31 is the peripheral region sa1.

The two inclined surfaces 34 are formed so as to include lines CL a distance (d/2) away from the two adjacent sides EL and to be plane-symmetric with respect to a plane orthogonal to the distal end surface 24a. An angle $\beta$ of the inclined surface 34 with respect to the distal end surface 24a satisfies $0°<\beta \leq 25°$. Namely, the angle $\beta$ of the inclined surface 34 is an angle in a range that is larger than 0 degrees and is 25 degrees or smaller with respect to a virtual distal end surface 24a on the rod lens 24. In other words, each peripheral region sa1 has the angle $\beta$ (second angle) that is larger than 0 degrees and is smaller than $(90-\alpha)$ with respect to the distal end surface 24a. By providing the two inclined surfaces 34 on the peripheral region sa1, it is possible to further expand the light distribution angle while restraining the decrease in the quantity of light.

It is preferable that the light distribution of the illumination light to be emitted from the peripheral region sa that is the light transmission region should be even as a whole.

In FIG. 11, when the distal end surface 24a is viewed in the direction orthogonal to the distal end surface 24a, the projected area (second area) of the inclined surface 31a on the distal end surface 24a is denoted by A, the projected area (second area) of the inclined surface 31b on the distal end surface 24a is denoted by B, the projected area (second area) of the inclined surface 31c on the distal end surface 24a is denoted by C, and the area (first area) of the peripheral region sa in a range of the distance (d/2) from the sides EL on the distal end surface 24a is denoted by D as shown in FIG. 11. The peripheral region sa has a triangular shape, and has a shape in which a central portion constituted by projected portions of the three inclined surfaces 31a, 31b, 31bc is excluded.

In other words, when the distance between the two parallel sides EL of two adjacent concave portions 31 is d, the region surrounded by virtual lines L2 the distance (d/2) away from the sides EL is the peripheral region sa (shown by oblique lines).

As shown in FIG. 11, the length of one side EL of the concave portion 31 is a, and the length of one side of the peripheral region sa is b.

For evening the two-dimensional light distribution of the illumination light to be emitted from the distal end surface 24a, it is preferable that a ratio r of D to A (or B or C) should be 1. When the ratio of D to A (or B or C) is 1, the quantity of light totally reflected by the inclined surfaces 31a, 31b, 31c and emitted from the peripheral region sa and the quantity of light not totally reflected by the inclined surfaces 31a, 31b, 31c and directly emitted from the peripheral region sa are equal, so that an even illumination is obtained.

However, practically, the ratio r does not need to be 1, and may be in a range of (⅓) to 3. In other words, it is preferable that (⅓)<r<3 should be satisfied. When the ratio r is a value beyond this range, an unbalance is generated between the quantity of light totally reflected by the inclined surfaces 31aa, 31b, 31c and emitted from the peripheral region sa and the quantity of light not totally reflected by the inclined surfaces 31a, 31b. 31c and directly emitted from the peripheral region sa, and the two-dimensional light distribution is not even, leading to an uneven illumination.

In other words, when the projected areas of each peripheral region sa and the inclined surface 31a (or 31b or 31c) on the distal end surface 24a when the distal end surface 24a is viewed in the perpendicular direction to the distal end surface 24a are denoted by D and A respectively, it is preferable that the ratio of D to A should be a value in a range that is larger than (⅓) and is smaller than 3.

A, B, C and D are expressed as Equations (1) and (2) described below.

$$A = B = C = \left(a \times \frac{a}{2} \times \sqrt{3} \times \frac{1}{2}\right) \times \frac{1}{3} = \frac{a^2}{4\sqrt{3}} \quad (1)$$

$$D = \frac{b^2}{4\sqrt{3}} - \frac{a^2}{4\sqrt{3}} \quad (2)$$

From Equations (1) and (2), Equation (3) described below is satisfied.

$$A:D = \frac{a^2}{4\sqrt{3}} : \frac{b^2 - a^2}{4\sqrt{3}} = a^2 : b^2 - a^2 \quad (3)$$

For example, for A=D, (b/a) is expressed as Equation (5), from Equation (4) described below.

$$\frac{D}{A} = \left(\frac{b}{a}\right)^2 - 1 = 1 \quad (4)$$

$$\frac{b}{a} = \sqrt{2} \quad (5)$$

Consequently, for example, for (⅓)<(D/A)<3, Expression (8) is obtained from Expressions (6) and (7) described below.

$$\frac{1}{3} < \left(\frac{b}{a}\right)^2 - 1 < 3 \quad (6)$$

$$\frac{4}{3} < \left(\frac{b}{a}\right)^2 < 4 \quad (7)$$

$$1.15 < \frac{b}{a} < 2 \quad (8)$$

Further, for example, when the distal end surface of the rod lens 24 is the ring-shaped distal end surface 24Aa shown in FIG. 8, it is preferable that a pitch Ep of each concave portion 31 should be in a range that satisfies Expression (9) described below. Here, φin is the inner diameter of the rod lens 24A having a cylindrical shape, and φout is the outer diameter of the rod lens 24A having a cylindrical shape.

$$\left(\frac{\phi_{out} - \phi_{in}}{2}\right) \times \frac{1}{100} < Ep < \left(\frac{\phi_{out} - \phi_{in}}{2}\right) \times \frac{1}{3} \quad (9)$$

Since the plurality of concave portions 31 described above are formed on the distal end surface 24a of the rod lens 24 and the peripheral regions sa are provided around the concave portions 31, light from the light guide 25 is diffused by the concave portions 31 on the distal end surface 24a of the rod lens 24 and the peripheral regions sa surrounding the concave portions 31. Particularly, light hitting against the three inclined surfaces 31a, 31b, 31c that are oblique surfaces of the concave portion 31 is emitted from the peripheral region sa that is the transmission region after the total reflection, and therefore, the decrease in the quantity of light is very small. Further, some of light from the proximal end surface 24b of the rod lens 24 is directly emitted from the peripheral region sa without being totally reflected by the concave portion 31.

Figure 14:
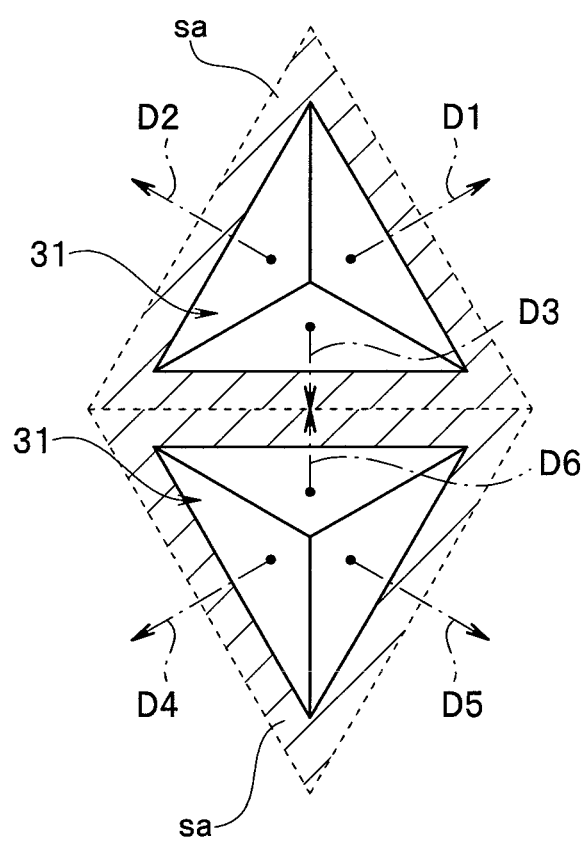
FIG. 14 is a diagram for describing light emission directions according to the embodiment of the invention.

Particularly, by two adjacent concave portions 31, light is diffused from the peripheral regions sa in a six directions. FIG. 14 is a diagram for describing light emission directions.

As shown in FIG. 14, in two adjacent concave portions 31, light reflected by the inclined surfaces 31a, 31b, 31c is emitted from the peripheral regions sa in six directions D1, D2, D3, D4, D5, D6, resulting in a little uneven light distribution.

Moreover, the shape of the opening of the concave portion 31 may be an isosceles triangle, a right triangle or the like, instead of a regular triangle.

As described above, in the embodiment, the light reflected by the inclined surfaces 31a, 31b, 31c is totally reflected, and is emitted from the peripheral regions sa. In the related art, the totally reflected light is return light, and is not emitted from the emission surface, leading to the loss of the quantity of light. However, according to the above-described configuration, it is possible to emit the totally reflected light without leakage, and to decrease the loss of the quantity of emitted light. Further, since the total reflected light is transmitted from the peripheral region sa, it is not necessary to decrease the angle of the inclined surfaces 31a, 31b, 31c for reducing the return light, and it is possible to maintain the largeness of the light distribution angle.

Consequently, according to the above-described embodiment, it is possible to provide an illumination optical system for endoscope that can expand the light distribution while reducing the quantity of the decrease in the quantity of emitted light.

Next, modifications of the above-described embodiment will be described.

(Modification 1)

In the above-described embodiment, since each concave portion 31 has a regular trigonal pyramid shape in which the bottom surface is at an upper portion and the apex is at a lower portion, the point 33 at the deepest portion is at the position of the barycenter of the regular triangle when the distal end surface 24a is viewed in the direction orthogonal to the distal end surface 24a, but the deepest portion of each concave portion may be at a position deviating from the barycenter when the distal end surface 24a is viewed in the direction orthogonal to the distal end surface 24a.

Figure 15:
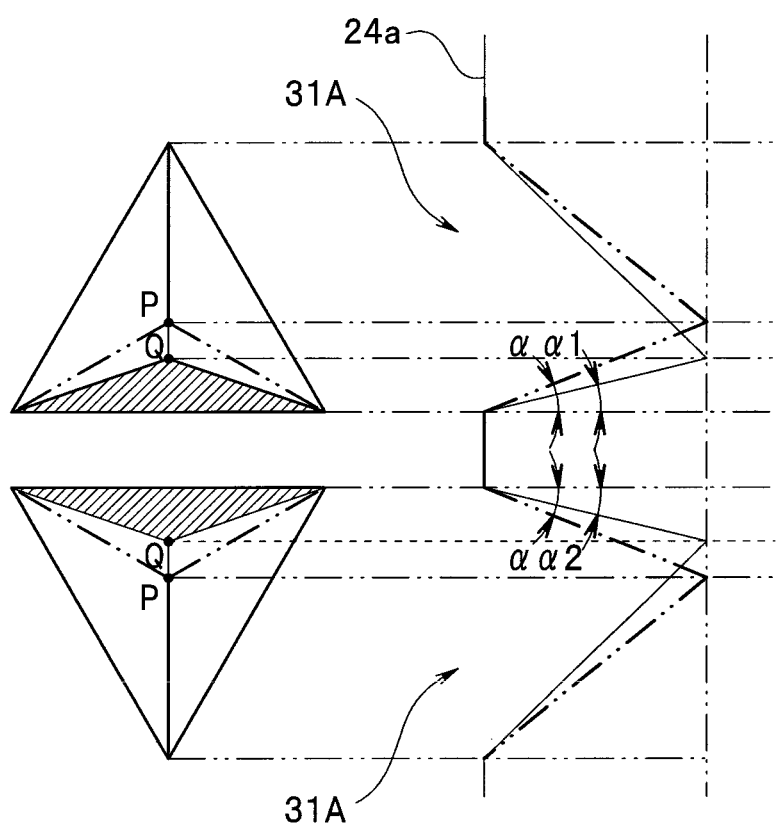
FIG. 15 is a diagram for describing a position of a deepest portion of a concave portion according to a modification 1 of the embodiment of the invention.

FIG. 15 is a diagram for describing the position of the deepest portion of a concave portion 31A according to a modification 1.

As shown in FIG. 15, the deepest portion of the concave portion 31A is positioned at a point Q deviating from a point P that is the barycenter position.

Therefore, inclination angles α1, α2 of two adjacent flat surfaces of two adjacent concave portions 31A shown in FIG. 15 are angles in a range that is larger than 3 degrees and is smaller than 20 degrees. In other words, 70°<(90−α1)<97° and 70°<(90−α2)<97° are satisfied. The inclination angles α1 and α2 may be the same or may be different.

It is possible to adjust the light distribution by changing the position of the deepest portion of the concave portion 31A. Alternatively, it is possible to adjust the light distribution by changing the inclination angles of the inclined surfaces 31a, 31b, 31c of the concave portion 31A.

As described above, also in the modification 1, it is possible to obtain the same effect as the effect in the above-described embodiment.

(Modification 2)

In the above-described embodiment and the modification 1, the concave portions 31, 31A have trigonal pyramid shapes, but the concave portion may have a quadrangular pyramid shape.

Figure 16:
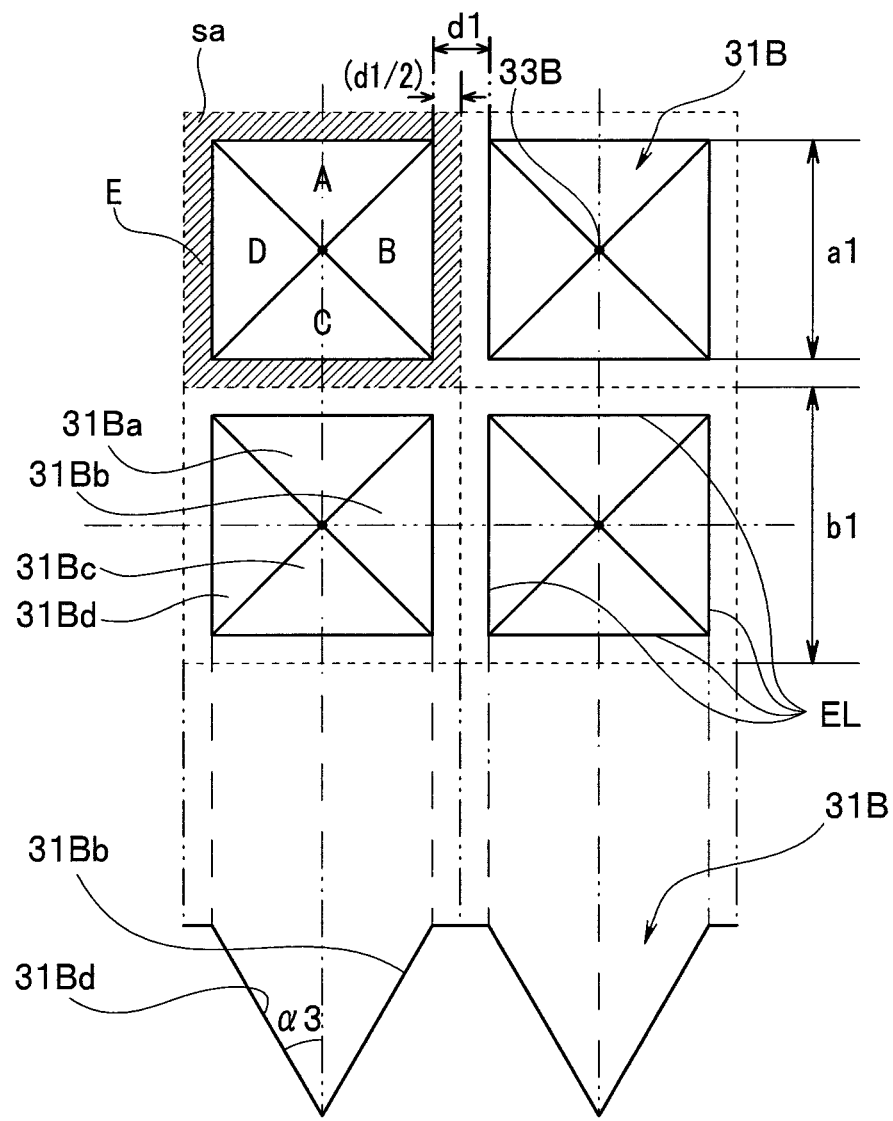
FIG. 16 is a diagram for describing a concave portion according to a modification 2 of the embodiment of the invention.

FIG. 16 is a diagram for describing a concave portion 31B according to a modification 2.

As shown in FIG. 16, each concave portion 31B has such a shape that a bottom surface having a quadrangular shape is parallel to the distal end surface 24a of the rod lens 24 when a physical object OB (not illustrated) having a regular quadrangular pyramid shape is fit in the concave portion 31B while the bottom surface is at an upper portion.

Consequently, the concave portion 31B includes four inclined surfaces 31Ba, 31Bb, 31Bc, 31Bd. The four inclined surfaces 31Ba, 31Bb, 31Bc, 31Bd have a square shape when the distal end surface 24a is viewed in the direction orthogonal to the distal end surface 24a. A point 33B where four border lines of pairs of two adjacent inclined surfaces are joined is at a deepest portion of the concave portion 31B. Angles of the inclined surfaces 31Ba, 31Bb, 31Bc, 31Bd with respect to the distal end surface 24a are equal.

In other words, each concave portion 31B has a quadrangular pyramid shape in which the apex is at the deepest portion and in which a square bottom surface is an opening, and the plurality of total reflection surfaces are four flat surfaces (inclined surfaces 31Ba, 31Bb, 31Bc, 31Bd) that are of the quadrangular pyramid shape and that are other than the bottom surface.

The opening of each concave portion 31B has a square shape. The opening includes four sides EL. A peripheral region sa (shown by oblique lines) is provided so as to surround the opening of each concave portion 31B. There is a transmission region having a width d1 between two parallel adjacent sides EL of two adjacent concave portions 31B. Two peripheral regions sa of the two adjacent concave portions 31B configure the transmission region between the two adjacent concave portions 31B.

In FIG. 16, when the distal end surface 24a is viewed in the direction orthogonal to the distal end surface 24a, the projected area of the inclined surface 31Ba on the distal end surface 24a is denoted by A, the projected area of the inclined surface 31Bb on the distal end surface 24a is denoted by B, the projected area of the inclined surface 31Bc on the distal end surface 24a is denoted by C, the projected area of the inclined surface 31Bd on the distal end surface 24a is denoted by D, and the area of the peripheral region sa in a range of a distance (d1/2) from the sides EL on the distal end surface 24a is denoted by E as shown in FIG. 16. The peripheral region sa has a quadrangular shape, and has a shape in which a central portion constituted by projected portions of the four inclined surfaces 31Ba, 31Bb, 31Bc, 31Bd is excluded.

In other words, when the distance between the two parallel sides EL of two adjacent concave portions 31B is d1, the region surrounded by virtual lines the distance (d1/2) away from the sides EL is the peripheral region sa (shown by oblique lines).

An inclination angle α3 of the inclined surfaces 31Ba, 31Bb, 31Bc, 31Bd with respect to the distal end surface 24a is an angle in a range from 5° to 25°. In other words, an angle (90−α3) of each total reflection surface with respect to the distal end surface 24a is an angle in a range that is smaller than 85 degrees and is larger than 65 degrees, and namely, 65°<(90−α3)<85° is satisfied.

As shown in FIG. 16, the length of the side EL of the concave portion 31B is a1, and the length of one side of the peripheral region sa is b1.

As described above, for evening the two-dimensional light distribution of the illumination light to be emitted from the distal end surface 24a, it is preferable that the ratio of E to A (or B or C or D) should be in a range of (⅓) to 3.

For example, A and E satisfy Equation (11) described below.

$$A:E = \left(\frac{1}{2} \times a1 \times \frac{a1}{2}\right) : b1^2 - a1^2 = \frac{a1^2}{4} : b1^2 - a1^2 \quad (11)$$

From Equation (11), Equation (12) described below is satisfied.

$$\frac{E}{A} = \frac{b1^2 - a1^2}{\left(\frac{a1^2}{4}\right)} = 4\left\{\left(\frac{b1}{a1}\right)^2 - 1\right\} \quad (12)$$

Consequently, in the case of (⅓)<(E/A)<3, a relation in Expression (13) described below is satisfied.

$$\frac{1}{3} < 4\left\{\left(\frac{b1}{a1}\right)^2 - 1\right\} < 3 \quad (13)$$

From Expression (13), Expression (14) is obtained.

$$\frac{1}{12} < \left\{\left(\frac{b1}{a1}\right)^2 - 1\right\} < \frac{3}{4} \quad (14)$$

From Expression (14), Expression (15) described below is satisfied.

$$\sqrt{\frac{13}{12}} < \frac{b1}{a1} < \frac{\sqrt{7}}{2} \quad (15)$$

Consequently, in the case where the concave portion has a quadrangular pyramid shape, it is preferable that the transmission region should meet a relation in Expression (15) described above.

As described above, also in the modification 2, it is possible to obtain the same effect as the effect in the above-described embodiment.

Note that the deepest portion may be at a position deviating from the barycenter in the modification 2 similarly to the modification 1. In other words, the point 33C at the deepest portion of the concave portion having a quadrangular pyramid shape may be at a position deviating from the barycenter of the square.

Figure 17:
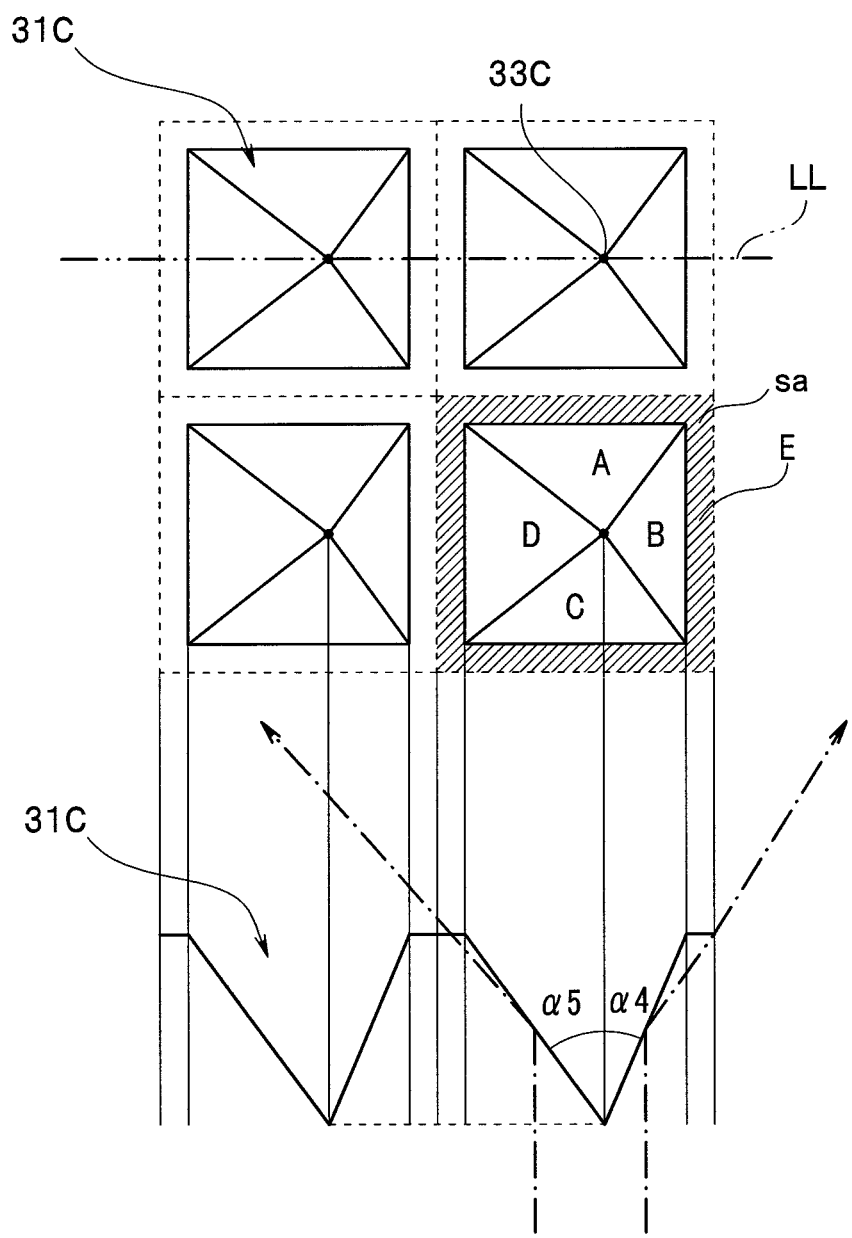
FIG. 17 is a diagram for describing a position of a deepest portion of a concave portion in which the deepest portion of the concave portion deviates from a barycenter of a square according to the modification 2 of the embodiment of the invention.

FIG. 17 is a diagram for describing a position of a deepest portion of a concave portion 31C in which the deepest portion of the concave portion deviates from the barycenter of the square. As shown in FIG. 17, the point 33C at the deepest portion of the concave portion 31C is at a position deviating from the barycenter position. A diagram at a lower portion in FIG. 17 shows a section of the distal end surface 24a along a two-dot chain line LL at an upper portion.

Therefore, inclination angles α4, α5 of two adjacent inclined surfaces of two adjacent concave portions 31C shown in FIG. 17 are angles in a range from 3 degrees to 20 degrees. In other words, 80°<(90−α4)<97° and 80°<(90−α5)<97° are satisfied. The inclination angles α4 and α5 may be the same or may be different.

In the case of FIG. 17, when the projected areas of inclined surfaces 31Ba, 31Bb, 31Bc, 31Bd on the distal end surface 24a when the distal end surface 24a is viewed in the direction orthogonal to the distal end surface 24a are denoted by A, B, C and D respectively, Expressions (16) and (17) described below are satisfied.

$$B < A = C < D \quad (16)$$

$$\frac{1}{3} \times B < E < 3 \times D \quad (17)$$

It is possible to adjust the light distribution in four directions by changing the position of the deepest portion of the concave portion 31C. Alternatively, it is possible to adjust the light distribution by changing the inclination angles of the inclined surfaces 31Ba, 31Bb, 31Bc, 31Bd of the concave portion 31C.

Moreover, the shape of the opening of the concave portion 31C may be a rectangle, instead of a square. In the case where the shape of the opening of the concave portion 31C is a rectangle, it is possible to further adjust the light distribution in four directions. Further, the position of a deepest portion of the rectangle may deviate from the barycenter.

As described above, also in the modification 2, it is possible to obtain the same effect as the effect in the above-described embodiment.

(Modification 3)

In the above-described embodiment and the modification 1, the concave portions 31, 31A have trigonal pyramid shapes, and in the modification 2, the concave portion 31B has a quadrangular pyramid shape, but the concave portion may have a hexagonal pyramid shape.

Figure 18:
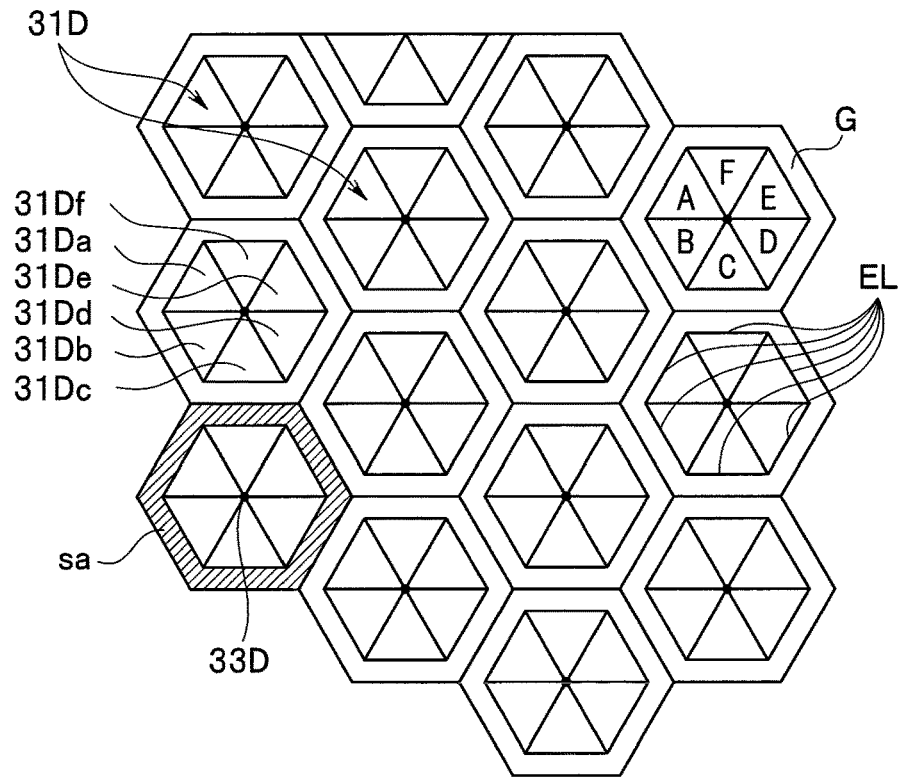
FIG. 18 is a diagram for describing a concave portion according to a modification 3 of the embodiment of the invention.
Figure 19:
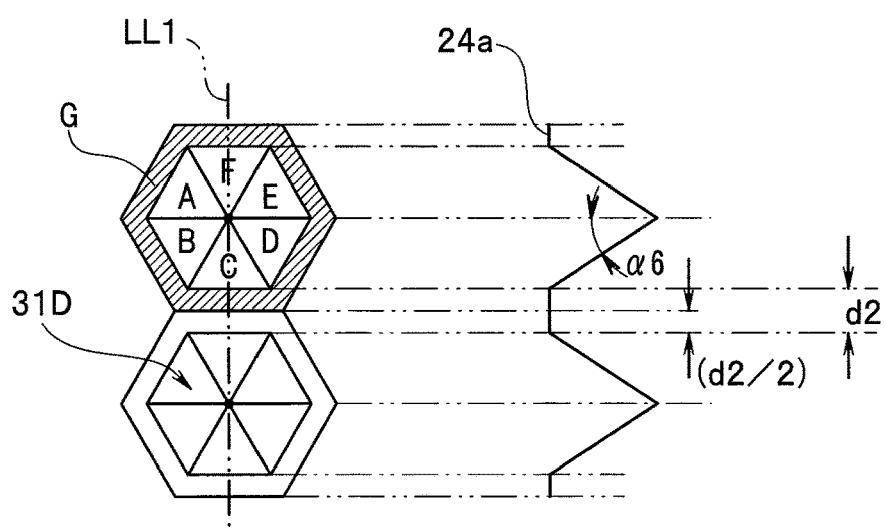
FIG. 19 is a diagram for describing the concave portion according to the modification 3 of the embodiment of the invention.

FIG. 18 and FIG. 19 are diagrams for describing a concave portion 31D according to the modification 3.

As shown in FIG. 18, each concave portion 31D has such a shape that a bottom surface having a hexagonal shape is parallel to the distal end surface 24a of the rod lens 24 when a physical object OB (not illustrated) having a regular hexagonal pyramid shape is fit in the concave portion 31D while the bottom surface is at an upper portion.

Consequently, each concave portion 31D includes six inclined surfaces 31Da, 31Db, 31Dc, 31Dd, 31De, 31Df. The six inclined surfaces 31Da, 31Db, 31Dc, 31Dd, 31De, 31Df have a regular hexagonal shape when the distal end surface 24a is viewed in the direction orthogonal to the distal end surface 24a. A point 33D where six border lines of pairs of two adjacent inclined surfaces are joined is at a deepest portion of the concave portion 31D. Angles of the inclined surfaces 31Da, 31Db, 31Dc, 31Dd, 31De, 31Df with respect to the distal end surfaces 24a are equal.

In other words, each concave portion 31D has a hexagonal pyramid shape in which the apex is at the deepest portion and in which the bottom surface having a regular hexagonal shape is an opening, and the plurality of total reflection surfaces are six flat surfaces (inclined surfaces 31Da, 31Db, 31Dc, 31Dd, 31De, 31Df) that are of the hexagonal pyramid shape and that are other than the bottom surface.

The opening of each concave portion 31D has a regular hexagonal shape. The opening includes six sides EL. A peripheral region sa is provided on the distal end surface 24a, so as to surround the opening of each concave portion 31D.

As shown in FIG. 19, there is a transmission region having a width d2 between two parallel sides EL of two adjacent concave portions 31D. A diagram on a right side in FIG. 19 shows a section of the distal end surface 24a along a two-dot chain line LL1 on a left side.

In FIG. 18 and FIG. 19, when the distal end surface 24a is viewed in the direction orthogonal to the distal end surface 24a, the projected area of the inclined surface 31Da on the distal end surface 24a is denoted by A, the projected area of the inclined surface 31Db on the distal end surface 24a is denoted by B, the projected area of the inclined surface 31Dc on the distal end surface 24a is denoted by C, the projected area of the inclined surface 31Dd on the distal end surface 24a is denoted by D, the projected area of the inclined surface 31De on the distal end surface 24a is denoted by E, the projected area of the inclined surface 31Df on the distal end surface 24a is denoted by F, and the area of the peripheral region sa in a range of a distance (d2/2) from the sides EL on the distal end surface 24a is denoted by G as shown in FIG. 19. The peripheral region sa has a hexagonal shape, and has a shape in which a central portion constituted by projected portions of the six inclined surfaces 31Da, 31Db, 31Dc, 31Dd, 31De, 31Df is excluded.

In other words, when the distance between the two parallel sides EL of two adjacent concave portions 31D is d2, the region surrounded by virtual lines the distance (d2/2) away from the sides EL is the peripheral region sa (shown by oblique lines).

An inclination angle α6 of the inclined surfaces 31Da, 31Db, 31Dc, 31Dd, 31De, 31Df with respect to the distal end surface 24a is an angle in a range from 3° to 20°. In other words, an angle (90−α6) of each total reflection surface with respect to the distal end surface 24a is an angle in a range that is smaller than 87 degrees and is larger than 70 degrees, and namely, 70°<(90−α6)<87° is satisfied.

Figure 20:
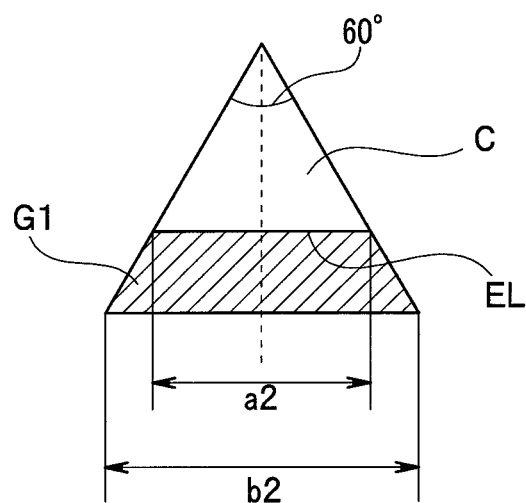
FIG. 20 is a plan view of an inclined surface and a part of a peripheral region according to the modification 3 of the embodiment of the invention.

FIG. 20 is a plan view of the inclined surface 31Dc and a part of the peripheral region sa. The length of one side EL of the concave portion 31D is a2, and the length of one side of the peripheral region sa is b2.

For example, an area C of a projected surface of the inclined surface 31Dc on the distal end surface 24a and an area G1 of the part of the peripheral region sa near the inclined surface 31Dc are expressed as Equations (21) and (22) described below, respectively.

$$C = \left(\frac{\sqrt{3}}{2}a2\right) \times a2 \times \frac{1}{2} = \frac{\sqrt{3}}{4}a2^2 \quad (21)$$

$$G1 = \frac{\sqrt{3}}{4}(b2^2 - a2^2) \quad (22)$$

From Equation (21) and Equation (22), the ratio of the area G of the peripheral region sa to the area C of the projected surface of the inclined surface 31Dc on the distal end surface 24a is shown by Equation (23) described below.

$$\frac{G}{C} = \frac{\frac{\sqrt{3}}{4}(b2^2 - a2^2) \times 6}{\left(\frac{\sqrt{3}}{4}a2^2\right)} = \frac{6(b2^2 - a2^2)}{a2^2} = 6\left(\left(\frac{b2}{a2}\right)^2 - 1\right) \quad (23)$$

As described above, for evening the two-dimensional light distribution of the illumination light to be emitted from the distal end surface 24a, it is preferable that the ratio of G to C (or A or B or D or E or F) should be in a range of (⅓) to 3.

From Equation (23), Expressions (24), (25) and (26) are obtained.

$$\frac{1}{18} < \left(\frac{b2}{a2}\right)^2 - 1 < \frac{1}{2} \quad (24)$$

$$\frac{19}{18} < \left(\frac{b2}{a2}\right)^2 < \frac{3}{2} \quad (25)$$

$$\sqrt{\frac{19}{18}} < \frac{b2}{a2} < \sqrt{\frac{3}{2}} \quad (26)$$

Consequently, in the case where the concave portion has a hexagonal pyramid shape, it is preferable that the peripheral region sa should meet a relation in Expression (26) described above.

As described above, also in the modification 3, it is possible to obtain the same effect as the effect in the above-described embodiment.

Note that the deepest portion may be at a position deviating from the barycenter in the modification 3 similarly to the modification 1. In other words, the point 33D at the deepest portion of the concave portion having a hexagonal pyramid shape may be at a position deviating from the barycenter of the regular hexagon.

(Modification 4)

The concave portions 31, 31A have trigonal pyramid shapes in the above-described embodiment and the modification 1, the concave portions 31B, 31C have a quadrangular pyramid shape in the modification 2, and the concave portion 31D has a hexagonal pyramid shape in the modification 3, but the concave portion may have a conical shape or a polygonal pyramid shape similar to the conical shape.

Also in the modification 4, it is possible to obtain the same effect as the effect in the above-described embodiment.

(Modification 5)

In the above-described embodiment and the modifications, the plurality of inclined surfaces 31a and others and the peripheral region sa in each concave portion are partitioned by three or more sides EL of the opening of the concave portion, but a flat surface portion or curved surface portion connecting the inclined surfaces 31a and others and the peripheral region sa may be provided between the inclined surfaces 31a and others and the peripheral region sa.

For example, a flat surface portion formed by beveling of parts of the sides EL may be between the inclined surfaces and the peripheral region sa. Furthermore, a plurality of flat surface portions may be between the inclined surfaces and the peripheral region sa.

Alternatively, a curved surface portion having a gentle curve connecting the inclined surfaces 31a and others and the peripheral region sa may be between the inclined surfaces and the peripheral region sa.

Also in the modification 5, it is possible to obtain the same effect as the effect in the above-described embodiment.

(Modification 6)

In the above-described embodiment and the modifications, the shapes of the plurality of concave portions formed on the distal end surface 24a are the same. However, without being limited to this, concave portions having different shapes may be formed on the distal end surface 24a in a mixed manner. For example, two concave portion regions including a region where a plurality of concave portions 31 having a trigonal pyramid shape are formed as the diffusion region DS and a region where a plurality of concave portions 31B having a quadrangular pyramid shape are formed as the diffusion region DS are provided on the distal end surface 24a that is the emission surface, and thereby, a plurality of concave regions different in the shape of the concave portion may be mixed on the distal end surface 24a.

Also in the modification 6, it is possible to obtain the same effect as the effect in the above-described embodiment.

(Modification 7)

In the above-described embodiment and the modifications 1 to 6, the diffusion structure (the diffusion region DS configured to diffuse the emitted light) is provided on the distal end surface 24a, 24Aa of the rod lens 24, 24A, but the diffusion structure may be provided on a separate member from the rod lens 24, 24A.

Figure 21:
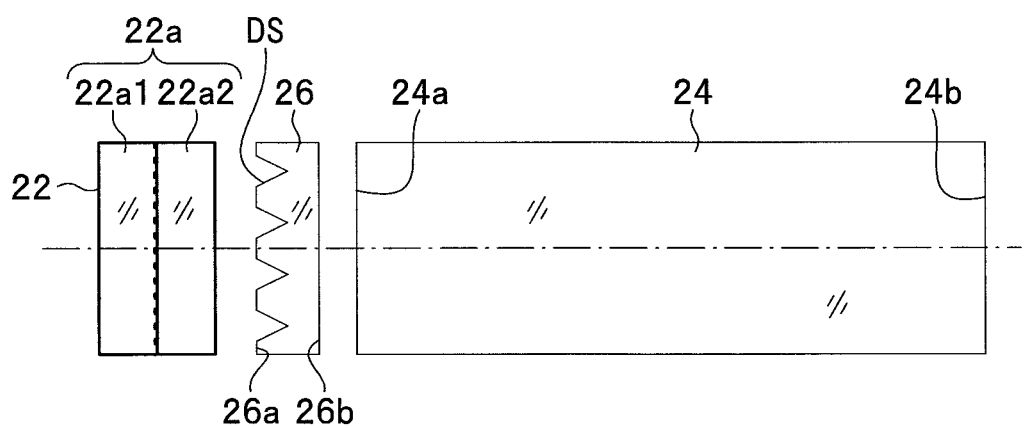
FIG. 21 is a diagram for describing a configuration on a light path for illumination light in an optical adaptor according to a modification 7 of the embodiment of the invention.

FIG. 21 is a diagram for describing a configuration on a light path for illumination light in an optical adaptor 10 according to a modification 7. The configuration including the cover glass 22a and the rod lens 24 will be described below as an example, but the same goes for the case of the configuration including the cover glass 22Aa and the rod lens 24A.

For example, a plate member 26 is disposed between the cover glass 22a and the rod lens 24. Note that the plate member 26 is arranged at a position away from the rod lens 24 in FIG. 21 but the plate member 26 may be bonded to the rod lens 24 using an adhesive or the like.

For example, the plate member 26 is molded from a transparent glass or a transparent plastic. The diffusion structure for diffusing the emitted light is formed on a distal end surface 26a of the plate member 26. As described above, the diffusion structure is configured as a diffusion region DS including a plurality of concave portions 31 (or concave portions 31A, 31B, 31C, 31D and others) and a plurality of peripheral regions sa (or peripheral regions sa1). By cutting the plate member 26 out of a large-sized material on which the diffusion structure is formed, a plurality of plate members 26 may be concurrently produced.

The light that enters the proximal end surface 24b of the rod lens 24 from the light guide 25 passes through the rod lens 24, is emitted from the distal end surface 24a of the rod lens 24, and enters a proximal end surface 26b of the plate member 26. The light passes through the plate member 26, is diffused by the diffusion region DS, is emitted from the distal end surface 26a, and enters the cover glass 22a.

Note that also in the modification 7, a grey surface (shown by a dotted line) may be provided on the cover glass 22a for eliminating the uneven light distribution, and the grey surface does not need to be provided when the securement of the quantity of light has priority over the elimination of the uneven light distribution.

Also in the modification 7, it is possible to obtain the same effect as the effect in the above-described embodiment, and it is not necessary to perform processing of providing the diffusion region DS on the distal end surface 24a of the rod lens 24, so that it is possible to use an existing rod lens 24.

(Modification 8)

In the above-described embodiment and the modifications 1 to 7, the illumination window 22 having an elongate semicircular shape shown in FIG. 2 or the illumination window 22A having a ring shape shown in FIG. 4 is provided. However, the shape of the illumination window is not limited to the shapes. As the illumination window, illumination windows having various shapes such as a circle, a polygon or a combination of a plurality of forms may be employed. Further, the number of illumination windows is not limited to one, and a plurality of illumination windows may be provided. As an example, two circular illumination windows may be provided.

Also in the modification 8, it is possible to obtain the same effect as the effect in the above-described embodiment, and the flexibility of the layout of the illumination window increases.

In the above-described embodiment and the modifications 1 to 8, the endoscope is a front-viewing endoscope, but the above-described embodiment and the modifications can also be applied to a side-viewing or oblique-viewing endoscope.

As described above, according to the above-described embodiment and the modifications, it is possible to provide an illumination optical system for endoscope, an optical adaptor and an endoscope that can expand the light distribution while reducing the quantity of the decrease in the quantity of emitted light.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An illumination optical system for use with an endoscope including an insertion portion configured to be inserted into a subject, the illumination optical system comprising:
    an optical element including an incident surface through which light enters as incident light and an emission surface configured to emit the light as illumination light,
    the emission surface includes a diffusion region configured to diffuse the light emitted,
    the diffusion region includes a plurality of concave portions and a plurality of peripheral regions, the plurality of concave portions and the plurality of peripheral regions being arrayed on the emission surface,
    each of the plurality of concave portions includes a plurality of total reflection surfaces inclined with respect to the emission surface, each of the plurality of total reflection surfaces being configured to totally reflect the incident light,
    at least one of the plurality of total reflection surfaces is inclined at a first angle with respect to the emission surface,
    each of the plurality of peripheral regions is formed so as to entirely surround the plurality of total reflection surfaces, and includes a transmission surface configured to transmit and emit:
        reflected light totally reflected by the plurality of total reflection surfaces after passing through the incident surface, and
        the incident light not totally reflected by the plurality of total reflection surfaces after passing through the incident surface.

2. The illumination optical system according to claim 1, wherein
    each of the plurality of concave portions has a trigonal pyramid shape in which an apex is farthest from the emission surface and in which a bottom surface closest to the emission surface having a regular triangular shape is an opening, and
    the plurality of total reflection surfaces are three flat surfaces that are of the trigonal pyramid shape and that are other than the bottom surface.

3. The illumination optical system according to claim 2, wherein an angle of each of the plurality of total reflection surfaces with respect to the emission surface is an angle between 85 degrees and 70 degrees, inclusive of 85 degrees.

4. The illumination optical system according to claim 1, wherein each of the plurality of peripheral regions is parallel to the emission surface.

5. The illumination optical system according to claim 1, wherein each of the plurality of peripheral regions has a second angle relative to the emission surface that is larger than 0 degrees and is smaller than the first angle.

6. The illumination optical system according to claim 1, wherein the plurality of concave portions are disposed on the emission surface such that two adjacent sides of two adjacent concave portions are parallel to each other.

7. The illumination optical system according to claim 1, wherein each of the plurality of peripheral regions and each of the plurality of total reflection surfaces when the emission surface is viewed in a perpendicular direction to the emission surface form a first area and a second area respectively, and a ratio of the first area to the second area is between $\frac{1}{3}$ and 3.

8. The illumination optical system according to claim 1, wherein
  each of the plurality of concave portions has a quadrangular pyramid shape in which an apex farthest from the emission surface and in which a square or rectangular bottom surface closest to the emission surface is an opening, and
  the plurality of total reflection surfaces are four flat surfaces that are of the quadrangular pyramid shape and that are other than the bottom surface.

9. The illumination optical system according to claim 8, wherein an angle of each of the plurality of total reflection surfaces with respect to the emission surface is an angle between 85 degrees and 65 degrees.

10. The illumination optical system according to claim 1, wherein
  each of the plurality of concave portions has a hexagonal pyramid shape in which an apex farthest from the emission surface and in which a bottom surface closest to the emission surface having a regular hexagonal shape is an opening, and
  the plurality of total reflection surfaces are six flat surfaces that are of the hexagonal pyramid shape and that are other than the bottom surface.

11. The illumination optical system according to claim 10, wherein an angle of each of the plurality of total reflection surfaces with respect to the emission surface is an angle between 87 degrees and 70 degrees.

12. The illumination optical system according to claim 1, wherein
  each of the plurality of concave portions has a polygonal pyramid shape in which an apex farthest from the emission surface and in which a bottom surface closest to the emission surface having a regular polygonal shape is an opening, and
  when the emission surface is viewed in a perpendicular direction to the emission surface, the apex is at a barycenter position of the regular polygon.

13. The illumination optical system according to claim 1, wherein
  the endoscope is a front-viewing endoscope, and
  in the optical element, the incident surface and the emission surface are parallel.

14. An optical adaptor comprising:
  an adapter body configured to be attached to a distal end portion of an insertion portion configured to be inserted into a subject;
  an optical element including an incident surface through which light enters as incident light and an emission surface configured to emit the light as illumination light,
  the emission surface includes a diffusion region configured to diffuse the light emitted,
  the diffusion region includes a plurality of concave portions and a plurality of peripheral regions, the plurality of concave portions and the plurality of peripheral regions being arrayed on the emission surface,
  each of the plurality of concave portions includes a plurality of total reflection surfaces inclined with respect to the emission surface, each of the plurality of total reflection surfaces being configured to totally reflect the incident light,
  at least one of the plurality of total reflection surfaces is inclined at a first angle with respect to the emission surface,
  each of the plurality of peripheral regions is formed so as to entirely surround the plurality of total reflection surfaces, and includes a transmission surface configured to transmit and emit
    reflected light totally reflected by the plurality of total reflection surfaces after passing through the incident surface, and
    the incident light not totally reflected by the plurality of total reflection surfaces after passing through the incident surface.

15. An endoscope comprising:
an illumination optical system; and
an insertion portion configured to be inserted into a subject, wherein
the illumination optical system includes an optical element including an incident surface through which light enters as incident light and an emission surface configured to emit the light as illumination light,
the emission surface includes a diffusion region configured to diffuse the light emitted,
the diffusion region includes a plurality of concave portions and a plurality of peripheral regions, the plurality of concave portions and the plurality of peripheral regions being arrayed on the emission surface,
each of the plurality of concave portions includes a plurality of total reflection surfaces inclined with respect to the emission surface, each of the plurality of total reflection surfaces being configured to totally reflect the incident light,
at least one of the plurality of total reflection surfaces is inclined at a first angle with respect to the emission surface,
each of the plurality of peripheral regions is formed so as to entirely surround the plurality of total reflection surfaces, and includes a transmission surface configured to transmit and emit
  reflected light totally reflected by the plurality of total reflection surfaces after passing through the incident surface, and
  the incident light not totally reflected by the plurality of total reflection surfaces after passing through the incident surface.

* * * * *